United States Patent
Osborn, III et al.

(10) Patent No.: US 6,635,799 B1
(45) Date of Patent: Oct. 21, 2003

(54) TOPSHEET FOR CONTACTING HYDROUS BODY TISSUES AND ABSORBENT DEVICE WITH SUCH A TOPSHEET

(75) Inventors: Thomas Ward Osborn, III, Cincinnati, OH (US); Christopher Bewick-Sonntag, Cincinnati, OH (US); Pamela Jean Brown, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

(21) Appl. No.: 09/637,440

(22) Filed: Aug. 11, 2000

Related U.S. Application Data

(63) Continuation-in-part of application No. 09/071,425, filed on May 1, 1998, now Pat. No. 6,270,486.

(51) Int. Cl.[7] ................................................. A61F 13/15
(52) U.S. Cl. .............................. 604/367; 604/385.101; 604/385.17
(58) Field of Search ....................... 604/385.17, 385.16, 604/385.01, 385.101, 367

(56) References Cited

U.S. PATENT DOCUMENTS

| | | |
|---|---|---|
| 4,846,824 A | 7/1989 | Lassen et al. |
| 5,762,644 A | 6/1998 | Osborn, III et al. |
| 5,891,126 A | 4/1999 | Osborn, III et al. |
| 5,916,205 A | 6/1999 | Olson et al. |
| 5,928,452 A | 7/1999 | McFall et al. |
| 5,951,537 A | 9/1999 | Osborn, III |
| 5,968,026 A | 10/1999 | Osborn, III et al. |
| 6,033,391 A | 3/2000 | Osborn, III et al. |
| 6,045,544 A | 4/2000 | Hershberger et al. |
| 6,261,277 B1 * | 7/2001 | Osborn, III et al. .... 604/385.17 |
| 6,316,688 B1 * | 11/2001 | Hammons et al. .......... 604/378 |
| 6,355,022 B1 * | 3/2002 | Osborn, III et al. .... 604/385.17 |
| 6,395,957 B1 * | 5/2002 | Chen et al. ................. 604/381 |
| 6,409,714 B2 * | 6/2002 | Osborn, III et al. .... 604/385.17 |
| 6,459,014 B1 * | 10/2002 | Chmielewski et al. ....... 604/360 |

* cited by examiner

Primary Examiner—Weilun Lo
Assistant Examiner—C L Anderson
(74) Attorney, Agent, or Firm—Kevin C. Johnson; Bridget D. Ammons; Jeffrey V. Bamber

(57) ABSTRACT

A body-contacting surface or topsheet for absorbent articles or devices that is comfortable when it is placed in contact with hydrous body tissues is disclosed. In one non-limiting embodiment, the topsheet is a non-absorbent, moderately hydrophilic to substantially hydrophobic nonwoven web. The topsheet can have a critical surface tension of less than or equal to about 45 dynes/cm. In one embodiment, the nonwoven web has been mechanically modified so that it is extensible in an amount greater than equal to about 30% under a force of 50 grams, and undergoes a caliper change of greater than or equal to about 30% under a pressure of 1,000 Pa after being subjected to a pressure of 250 Pa. The topsheet is placed on absorbent devices such as sanitary napkins, tampons, pantiliners, interlabial devices, incontinence devices, bandages, and other types of articles. A method of capturing discharges from a source of discharges on a wearer's body in which at least a portion of the source of discharges is located within hydrous membranes having irregular surfaces (e.g., a female wearer's interlabial or intervaginal space) is also disclosed.

11 Claims, 9 Drawing Sheets

TOPSHEET FOR CONTACTING HYDROUS BODY TISSUES AND ABSORBENT DEVICE WITH SUCH A TOPSHEET

This application is a continuation-in-part of application Ser. No. 09/071,425 filed May 1, 1998, now U.S. Pat. No. 6,270,486.

FIELD OF THE INVENTION

This invention relates to an improved body-contacting surface or topsheet for absorbent articles, bandages, or other such devices, and more particularly to a topsheet that is comfortable when it is placed in contact with hydrous body tissues. The present invention also relates to absorbent devices such as sanitary napkins, tampons, pantiliners, interlabial devices, incontinence devices, and bandages, which have such a topsheet. An improved absorbent structure for an absorbent article is also disclosed. The present invention further relates to a method of capturing discharges from a source of discharges on a wearer's body in which at least a portion of the source of discharges is located within hydrous membranes having irregular surfaces (e.g., a female wearer's interlabial or intervaginal space).

BACKGROUND OF THE INVENTION

All manner and variety of absorbent articles configured for the absorption of body fluids such as menses, urine and feces are well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953; U.S. Pat. No. 4,631,062, entitled "Labial Sanitary Pad", issued to Lassen, et al. on Dec. 23, 1986; and U.S. Pat. No. 4,673,403, entitled "Method and Pad Allowing Improved Placement of Catamenial Devices", issued to Lassen, et al. on Jun. 16, 1987.

Interlabial pads have the potential to provide even greater freedom from inconvenience because of their small size and reduced risk of leakage. Numerous attempts have been made in the past to produce absorbent devices which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is the INSYNC Miniform interlabial pad which is marketed by A-Fem of Portland, Oreg. and described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available IN-SYNC interlabial device suffers from the disadvantage that it may tend to allow by-pass flow around its edges. Such flow can cause body soiling or panty soiling which many consumers find unacceptable.

Improved interlabial devices are described in the following patents assigned to The Procter & Gamble Company: U.S. Pat. Nos. 5,762,644; 5,885,265; 5,891,126; 5,895,381; 5,916,205; 5,928,452; 5,951,537; 5,968,026; 6,033,391; and, 6,045,544. The search for improved interlabial devices has, however, continued. In particular, there is a need for improved, more comfortable, topsheets for such devices that contact the wearer's inner labia majora surfaces, and the skin within the vaginal vault.

Products that are to be worn predominantly interlabially are expected to remain in place without any of the usual panty attachment approaches (i.e., adhesives). In order for such products to remain positioned within the labia they are required to adapt to the labial vault and remain fixed via a combination of structural adaptation (i.e. fit) and physical interactions such as friction (i.e. slippage control) or adhesion due to capillary suction.

Products that are worn interlabially are predominantly worn within the labial vault and enclosed by the labia minora and the labia majora. Anatomically speaking, there are striking differences in both physical structure and the properties of the skin within the labia, particularly the labia minora compared to adjacent skin surfaces such as in the perineal groove, buttocks and inner thigh regions that would normally be contacted by a sanitary napkin. It is important to differentiate between external surfaces (such as the buttocks, perineal grove, the outwardly facing labia majora surfaces) and internal surfaces (such as the labia minora, vulva vault, and the vagina). As one progresses from the "external" bodily surfaces of the buttocks or inner thighs, representative of a normal stratum cornea, towards the vulva the stratum cornea begins to change. The vulva majora (externally facing surfaces) still exhibits a stratum cornea but somewhat thickened and in a somewhat immune sensitized state indicative of a greater sensitivity to external influence. Nevertheless, such "external" skin types, macroscopically viewed, are still considered to be relatively smooth and dry to the touch. They are considered to be relatively hydrophobic in nature. They exhibit similar degrees of hydration to other bodily sites, similar friction coefficients (especially when absorbent materials are next to these tissues) and degrees of elasticity and compressibility that are all within a factor of three (see Elsner et al., *British Journal of Dermatology* (1990). Issue 122, p 607–614, and Elsner et al., *Dermatologica* (1990). Issue 181, p 88–91). Moving interlabially from the labia majora (moving to the internal bodily surfaces) to the labia minora and then internally (vaginal vault) a fundamental change in the properties of the skin or labial membrane occurs. The inner labial minora surfaces are starting to become more characteristic of a mucosa membrane than a stratum cornea. As one moves from the labial vault into the vaginal vault the transition is complete to a mucosa membrane. Tissues within the labial vault, especially the inward facing surfaces of the labia minora are permanently wet, are believed to have a significantly higher friction coefficient, elasticity, and compressibility. These membranes are highly textured (irregular surface) and are hydrophilic not hydrophobic.

Traditionally, on externally worn absorbent articles (contacting predominantly "external" bodily surfaces) such as sanitary napkins, a hydrophilic topsheet or hydrophobic topsheets treated to be hydrophilic (such as with a surfactant) have been utilized to ensure adequate absorption and transmission of bodily discharges to the absorbent core structure. There has been a significant number of disclosures on approaches to create soft, performing topsheets for use externally and in contact with dry and relatively smooth skin surfaces such as in the perineal groove, buttocks and inner thigh regions.

In the case of internally worn disposable absorbent products (contacting predominantly "internal" bodily surfaces, traditionally absorbent and hydrophilic topsheets and particularly rayon based topsheets (delivering biodegradability and softness) have been chosen such that the products can be disposed of by flushing down a toilet. Such topsheets (particularly rayon webs) have also been utilized for hybrid absorbent products that are either partially or wholly worn within the labial vault. However, the applicants have discovered that traditional hydrophilic and particularly absorbent hydrophilic topsheets are not ideally suited for internal and particularly interlabially worn absorbent products, and in fact may contribute significantly to discomfort and perceptions of soreness and irritation while wearing such products in use. This seems to be contrary to the known art that would expect soft, smooth, hydrophilic topsheets such as rayon or many nonwovens to be ideal candidates for a general feminine absorbent article.

This conflict with prior art can perhaps be understood if we consider an interlabially worn absorbent pad with an absorbent, hydrophilic topsheet such as a rayon web. On placing such a product within the labia and specifically in contact with the "internal" facing surfaces of the labial minora, such topsheets are able to absorb labial secretions. Apart from tending to dry the labial membrane (one source of discomfort and irritation) the topsheet has a natural tendency to adhere to the labial membrane via hydrophilic-hydrophilic compatibility. This establishes yet another source of discomfort as the labial membrane is very elastic and is expected to deform/freely move with bodily motion and with respect to each other. If an absorbent product is attaching to this membrane and is unable to move to the same degree of elasticity, a process of adhere-sheer is set up during bodily motion that creates a level of discomfort (rough, dry rubbing sensations) for the products user.

Several approaches have been attempted to provide improved, more comfortable topsheets for such products. European Patent Application 0 685 215 A1 is directed to a "Vaginal moisture balanced tampon and process." This publication is directed toward reducing vaginal epithelium drying by reducing the capillary suction pressure of a tampon in early use. This is said to be accomplished by modifying the capillary suction pressure of the surface of the tampon by using hydrophobic components in the tampon, such as hydrophobic fibers and/or a hydrophobic cover material. Other means of obtaining a lower capillary suction pressure are said to include increasing the denier of the fibers in the tampon's absorbent core and/or decreasing the density of the tampon.

U.S. Pat. No. 4,846,824, Lassen, et al., entitled "Labial Sanitary Pad" describes another approach. The Lassen '824 patent indicates that the use of a physiologically hydrous cover maintains the ideal level of moisture within the urogenital region. The term "physiologically hydrous" is said to connote a cover material that maintains a suitably moist interface between the tissues of the vestibule and the pad when disposed in the vestibular environment. An example of a highly preferred cover in the Lassen '824 patent is one made from a spunlaced polyester such as that sold under the tradename "SONTARA" by E. I. DuPont Company.

Therefore, a need exists for improved devices which are worn adjacent to a wearer's hydrous body tissues, such interlabial device which will reduce the incidence of body and panty soiling when used. In particular, a need exists for improved, more comfortable, topsheets for such devices that contact the wearer's inner labia majora surfaces, and the skin within the vaginal vault. Such a device should be easy to insert and be comfortable during wear. Preferably, such a device will be comfortable enough for everyday use, if desired. A need also exists for an improved interlabial device which has sufficient capacity to serve as a stand alone product during the heavy flow days of a wearer's menstrual period, and is not subject to the problem of falling out of the interlabial space when loaded to its absorbent capacity. A need also exists for other types of absorbent devices such as sanitary napkins, tampons, pantiliners, interlabial devices, incontinence devices, and bandages, which have such a topsheet.

SUMMARY OF THE INVENTION

The present invention relates to an improved body-contacting surface or topsheet for absorbent devices that come into contact with a wearer's hydrous body tissues. These hydrous body tissues may include, but are not limited to hydrous tissues such as interlabial skin or tissue and mucosal tissues such as vaginal tissues. In one non-limiting embodiment, the topsheet comprises a non-absorbent, moderately hydrophilic to substantially hydrophobic nonwoven web. The topsheet can have a critical surface tension of less than or equal to about 45 dynes/cm, preferably less than or equal to about 40 dynes/cm. In one embodiment, the nonwoven web has been mechanically modified so that it is extensible in at least one direction in an amount greater than or equal to about 30% under a force of 50 grams. The topsheet preferably undergoes a caliper change of greater than or equal to about 30% under a pressure of 1,000 Pa after being subjected to a pressure of 250 Pa. The topsheet is placed on absorbent devices such as sanitary napkins, tampons, pantiliners, interlabial devices, incontinence devices, bandages, and other articles.

The present invention also relates to absorbent devices such as sanitary napkins, tampons, pantiliners, interlabial devices, incontinence devices, bandages, and other articles which have such an improved topsheet. The term "interlabial device" refers to an absorbent device that is at least partially insertable into the interlabial space of a female wearer for catamenial purposes (including menses and mid-cycle discharges), incontinence protection (including urine), or both.

The present invention further relates to a method of capturing discharges from a source of discharges on a wearer's body in which at least a portion of the source of discharges is located within hydrous membranes having irregular surfaces (e.g., a female wearer's interlabial or intervaginal space). The method comprises: providing an absorbent article having a liquid pervious top surface structure, said top surface structure having a body contacting surface, wherein said top surface structure has at least regions that are extensible; and placing the absorbent article adjacent to the hydrous membranes of a wearer's body, with the body-contacting surface of the top surface structure at least partially in contact with the hydrous membranes.

The absorbent device utilizing the topsheet can be of any suitable structure known in the art, or it may be of a novel structure. The absorbent interlabial device, in one non-limiting embodiment, is a small pad-like structure that comprises a liquid pervious topsheet, a liquid impervious backsheet which is joined to the topsheet, and an absorbent core positioned between the topsheet and backsheet. The device preferably comprises an axis of preferred bending, preferably located generally along the longitudinal center-line of the device. When the device is folded along this axis and inserted into the wearer's interlabial space, the topsheet maintains contact with the walls of the wearer's labia. Preferably, the device comprises biodegradable materials. In some embodiments, the backsheet of the absorbent interlabial device is water dispersible. In other embodiments, the backsheet can be eliminated. The backsheet can be eliminated if the underside of the absorbent core is coated. Alternatively, the backsheet can be eliminated if the device is primarily contained within the labia, and the interlabial device is folded along a longitudinal axis. In such a case, the device assumes an inverted V or U-shaped cross-sectional structure, and the portions of the device which would normally be provided with a backsheet will face inward toward each other, and will not contact a wearer's garments. The elimination of a backsheet will improve the breathability of the device. A tab may be joined to the underside of the device to facilitate insertion and optional removal of the device with the fingers.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
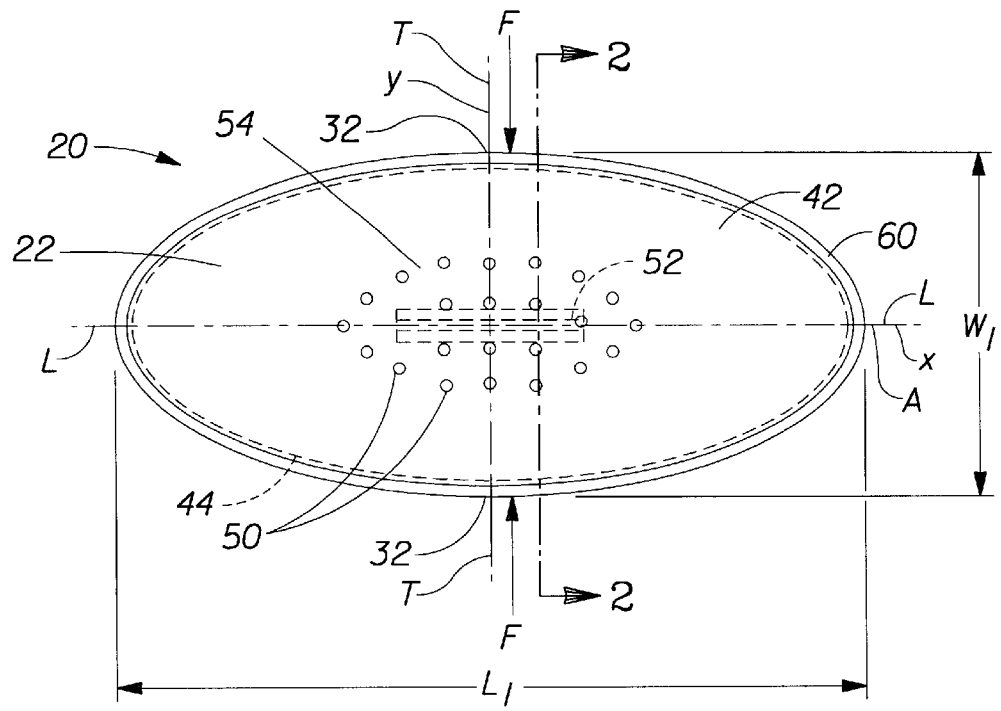
FIG. 1 is a top plan view of a preferred embodiment of the absorbent interlabial device according to the present invention.

The present invention relates to an improved body-contacting surface or topsheet for absorbent articles or devices, and more particularly to a topsheet that is comfortable when it is placed in contact with hydrous body tissues. The present invention also relates to absorbent devices such as sanitary napkins, tampons, pantiliners, interlabial devices, and incontinence devices, which have such a topsheet. The present invention further relates to a method of capturing discharges from a source of discharges on a wearer's body in which at least a portion of the source of discharges is located within hydrous membranes having irregular surfaces (e.g., a female wearer's interlabial or intervaginal space).

FIGS. 1–5 show one non-limiting example of an absorbent interlabial device, interlabial device 20 that may be provided with the improved topsheet 42 described herein. The present invention, however, is not limited to use on a structure having the particular configuration shown in the drawings.

As used herein, the term "absorbent interlabial device" refers to a structure which has at least some absorbent components, and which is specifically configured to reside at least partially within the interlabial space of a female wearer during use. Preferably, when the absorbent interlabial device 20 is properly sized for an individual wearer, at least about half of the entire absorbent interlabial device 20 of the present invention resides within such interlabial space. More preferably, substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

Figure 2:
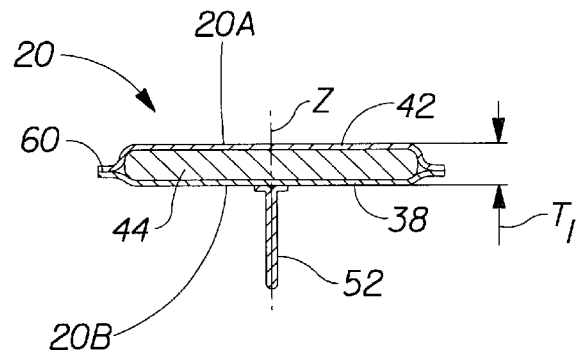
FIG. 2 is a cross sectional view of the absorbent interlabial device shown in FIG. 1, taken along line 2—2 of FIG. 1.

The absorbent interlabial device 20 shown in FIG. 1 has a longitudinal centerline L which runs along the "x" axis. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line, axis, or direction that is generally perpendicular to the longitudinal direction. The lateral direction is shown in FIG. 1 as the "y" direction. The absorbent interlabial device 20 shown in FIG. 1 also has a transverse centerline T. The "z" direction, shown in FIG. 2, is a direction parallel to the vertical plane described above. The term "upper" refers to an orientation in the z-direction toward the wearer's head. "Lower" or "downwardly" is toward the wearer's feet.

Figure 3:
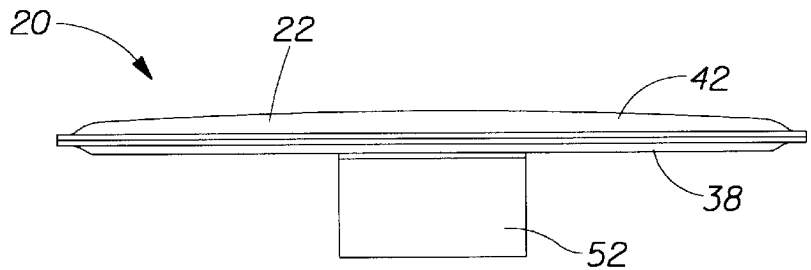
FIG. 3 is a side view of the absorbent interlabial device shown in FIG. 1.

The interlabial device 20 shown in FIGS. 1–3 is in one preferred configuration. The interlabial device 20 has a body-facing (or "body-contacting" side) 20A and an opposed underside 20B. The interlabial device comprises a pad-like main body portion (or "central absorbent portion") 22 and an optional placement and removal tab 52 which is joined to the underside 20B of the main body portion 22 to provide the overall interlabial device with a "T"-shaped cross-sectional configuration. The main body portion 22 can be in any suitable configuration. Non-limiting examples of shapes for the main body portion 22 when viewed from the top as in FIG. 1 include ovoid, elliptical, trapezoidal, rectangular, triangular, diamond-shaped, or any combination of the above. As shown in FIG. 1, the preferred plan view shape for the main body portion 22 and the overall absorbent interlabial device 20 is generally ovoid or elliptical. The plan view shape of the main body portion 22 tapers from the transverse centerline T towards its front and rear ends. The main body portion 22, in this embodiment, is relatively flat in its side profile, but may taper slightly from front to rear as shown in FIG. 3.

As shown in FIGS. 1–2, the interlabial device preferably comprises a liquid pervious topsheet 42, a liquid impervious backsheet 38 joined to the topsheet 42, and an absorbent core 44 positioned between the topsheet 42 and the backsheet 38. The interlabial device 20 is preferably of a size and shape that allows at least the majority of the device 20 to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is important to its comfort and effectiveness. The length of the absorbent interlabial device 20 is measured along the longitudinal centerline L in the longitudinal direction (or "x"-direction). The absorbent interlabial device 20 preferably has a length $L_1$ which is greater than about 60 mm and less than about 130 mm. More preferably, the length $L_1$ is between about 70 mm and about 105 mm. The width of the interlabial device 20 is measured along the transverse centerline T in the transverse direction (or "y"-direction). The absorbent interlabial device 20 preferably has a width $W_1$ which is between about 25 mm and about 50 mm. The thickness (or caliper) is the "z"-direction dimension of the main body portion of the device 20. Caliper measurements given herein were measured using an AMES gauge with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper $T_1$ of the main body portion of the absorbent interlabial device 20 is preferably less than the width $W_1$ and the length $L_1$ of the device 20. Preferably, the caliper $T_1$ of the main body portion of the absorbent interlabial device 20 is less than or equal to about 8 mm, more preferably the caliper $T_1$ is less than or equal to about 6 mm, and even more preferably the caliper is less than or equal to about 4 mm.

The main body portion 22 of the interlabial device 20 is preferably also flexible, more preferably relatively highly flexible, but not so flexible that it will be difficult to insert. This will increase the wearing comfort of the interlabial device 20. The main body portion 22 of the interlabial device 20 preferably has a flexure resistance within the ranges disclosed in U.S. Pat. No. 5,951,537 issued to Osborn on Sep. 14, 1999.

Construction of the absorbent interlabial device 20 according to the particular size parameters given above results in a product with increased comfort and effectiveness compared to previous interlabial devices. For example, many women find interlabial pads which are shorter than the absorbent interlabial device 20 described herein to be difficult to position properly within the interlabial space. Even if such pads are positioned properly, they have an increased tendency to allow by-pass flow of body exudates around the edges of the pad.

The interlabial device 20 is preferably provided with sufficient absorbency to absorb and retain the exudates discharged from the wearer's body. The capacity of the product, however, is dependent at least partially upon the physical volume of the absorbent interlabial device 20. The absorbent interlabial device preferably has a capacity of at least about 1 g of 0.9% by weight saline solution, and may have a capacity of up to about 30 g by using absorbent gels or foams that expand when wet. Preferably, capacities typically range from about 2 to about 12 grams, for saline. More preferably, the capacity of the device 20 is greater than or equal to about 6 g for saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, particularly if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The individual components which may be suitable for the various embodiments of the interlabial device 20 will now be looked at in greater detail with reference to FIGS. 1–3.

The topsheet 42 comprises a first liquid pervious component. The topsheet 42 is liquid pervious, permitting liquids (e.g., menses and/or urine) to readily penetrate through its thickness. It should be understood that when the topsheet 42 is described herein as being liquid pervious, if the topsheet is not liquid pervious on its own, this liquid perviousness will be considered to be present if the topsheet is used in conjunction with another layer, such as an underlying layer which draws liquids through the topsheet. The topsheet 42 should be compliant, soft feeling, and non-irritating to the wearer's skin. In particular, a topsheet which is used on absorbent devices that come into contact with a wearer's hydrous body tissues, should even be more comfortable. These hydrous body tissues may include, but are not limited to hydrous tissues such as interlabial skin or tissue and mucosal tissues such as vaginal tissues.

A suitable topsheet 42 may be manufactured from a range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., hydrophobically-treated wood, rayon, or cotton fibers), synthetic fibers (e.g., polymeric fibers such as polyester, rayon, polypropylene, or polyethylene fibers) or from a combination of natural and synthetic fibers. If the topsheet comprises a nonwoven material, it can be made by any suitable process. For example, it can be carded, spunbonded, etc.

The topsheet materials described above (woven, nonwoven, films, etc.) can be made from biodegradable materials, or non-biodegradable materials. As used herein, the term "biodegradable materials" refers to materials having greater than or equal to about 70% biodegradation (percentage of theoretical carbon dioxide evolution) after 28 days when measured according to the Sturm Test which has been designated Method 301B by the Organization for Economic Cooperation and Development, 2 rue Andre Pascal, 75775 Paris Cedex 16, France. Preferably, the materials comprising the interlabial device of the present invention have a biodegradation of greater than about 80% and, more preferably, biodegradation is greater than or equal to about 90%.

The topsheet 42 should be provided with the improved properties described herein so that it will be more comfortable for contacting the wearer's hydrous body tissues. The topsheet preferably comprises a non-absorbent, moderately hydrophilic to substantially hydrophobic material. The topsheet preferably has a critical surface tension of less than or equal to about 45 dynes/cm, more preferably less than or equal to about 40 dynes/cm. The critical surface tension should be measured according to the Material Critical Surface Tension test in the Test Methods section. In preferred embodiments, the topsheet is made as hydrophobic as possible to reduce the tendency for it to adhere to the hydrous body tissues.

The topsheet 42 should preferably be compressible and resilient so that it is comfortable when placed adjacent to the wearer's hydrous body tissues. The compressibility is preferably measured under loads typically encountered when wears a product having the topsheet thereon. The topsheet preferably undergoes a caliper change of greater than or equal to about 30% under a pressure of 1,000 Pa after being subjected to a pressure of 250 Pa. The topsheet 42 preferably undergoes an absolute caliper change of greater than or equal to about 0.15 mm under a pressure of 1,000 Pa after being subjected to a pressure of 250 Pa. The topsheet compressibility should be measured using the Topsheet Compressibility (Thickness Change) test described in the Test Methods section.

The topsheet 42 is preferably also extensible so that it will be capable of extending with the movements of the wearer's body, and specifically with the movements of the wearer's hydrous body tissues. Anatomically speaking, the wearer's labia resides in a relatively low motion zone of the body. Even though the extent the labia is expected to elongate as a result of motion is relatively low, due to the high extensibility of the labial membrane, the topsheet preferably elongates as required with minimal forces. The topsheet is preferably extensible in at least one direction in an amount greater than or equal to about 30% under a force of 50 grams. The topsheet 42 may be extensible in one direction, in two directions, in multiple directions, or in all directions (i.e., it may be omni-directionally extensible).

In other embodiments, a topsheet 42 may be provided which is comfortable when one of the qualities quantified herein is lower than set forth herein, if one of the other qualities of the topsheet quantified herein is increased. For instance, in one non-limiting example, the topsheet 42 may have a different combination of compressibility and extensibility, if desired. For example, a suitable topsheet may have an extensibility in at least one direction of greater than or equal to about 20% under a force of 50 grams, and the topsheet may undergo a caliper change of greater than or equal to about 40% when tested according to the Topsheet Compressibility/Thickness Change Test.

The starting materials (or base materials) described above may need to be altered or modified (mechanically, chemically, or otherwise) to provide them with these properties.

Figure 6:
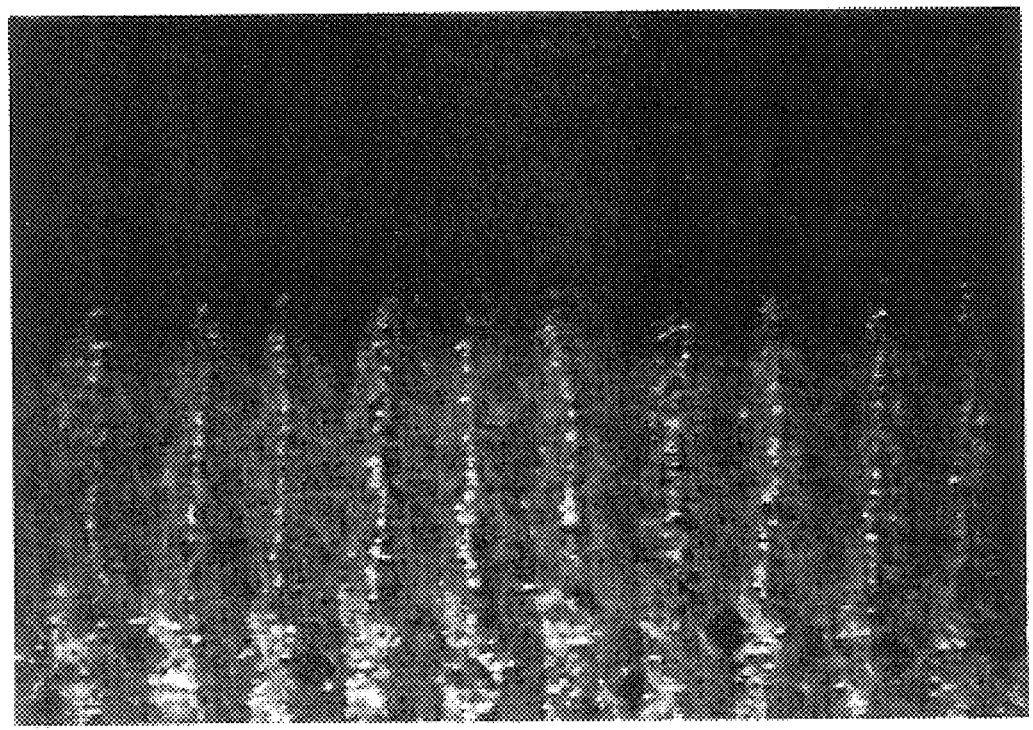
FIG. 6 is a photomicrograph of a portion of one embodiment of a topsheet according to the present invention.

In one embodiment, the topsheet can be formed of a web that has been mechanically modified to provide it with these properties. FIG. 6 shows one suitable topsheet 42 for use in the present invention. The topsheet shown in FIG. 6 is a mechanically altered spunbonded nonwoven material comprised of polethylene fibers which has a basis weight of 23 grams/m$^2$. The fibers preferably have a relatively fine denier, preferably less than or equal to about 5, more preferably less than or equal to about 3. One preferred base material having these properties, is known as COROLIND nonwoven material, which is obtained from BBA Nonwovens (formerly Corovin GmbH) of Piene, Germany under the tradename PE HPC-2, code T23FOR. Such a material is then mechanically altered as described herein. Another suitable topsheet 42 can be a mechanically altered nonwoven web comprised of BIONELLE 3001 biodegradable fibers obtained from Showa Hugh Polymer Co. of Tokyo, Japan. These nonwoven materials can be mechanically altered by ring rolling or by forming a strainable network therein to form the topsheet 42.

In the embodiment shown in FIG. 6, the nonwoven material is mechanically altered by forming a strainable network therein. The strainable network is formed by a process which may be referred to herein as forming the topsheet base material into a stretchable elastic-like film (or "SELFing" the topsheet base material). This acronym will be used, although in the present case, it is to be understood that the topsheet base material (and the structure formed by SELFing the same) are not limited to films. That is, other materials, such as nonwovens can be subjected to the process for forming a strainable network therein.

Figure 7:
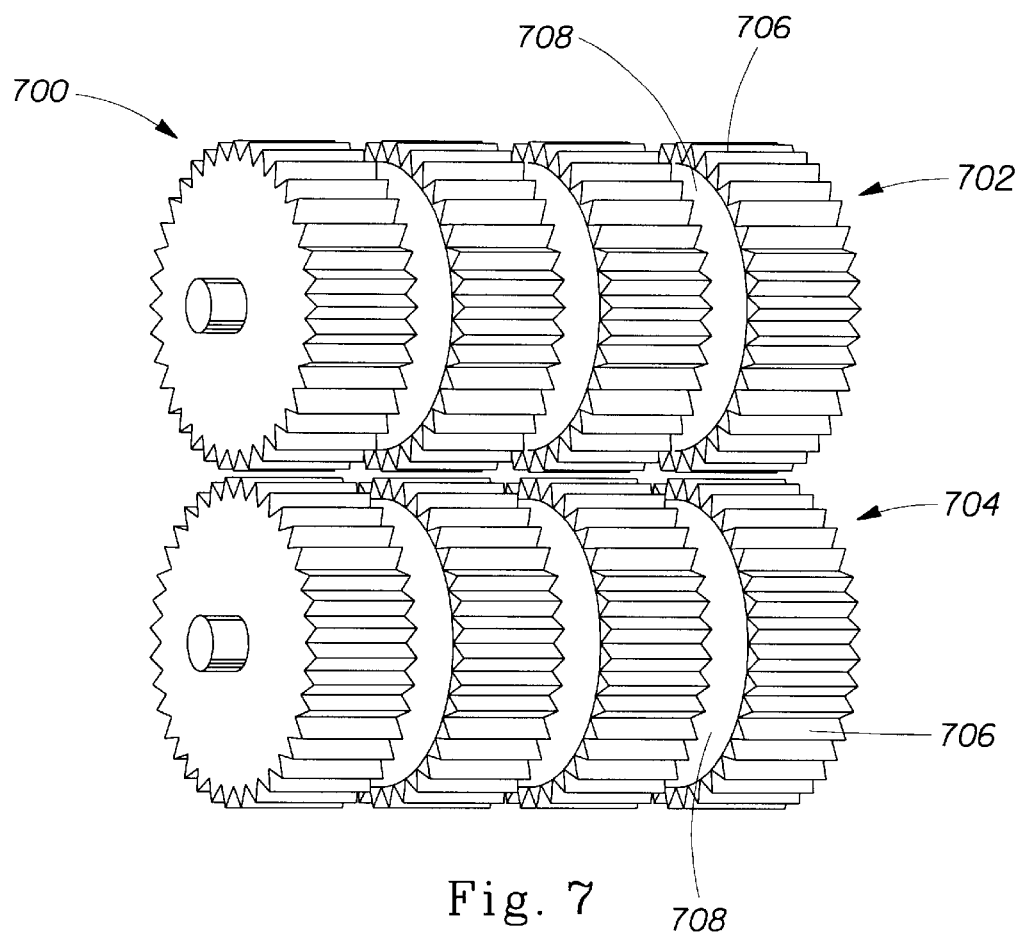
FIG. 7 is a simplified illustration of an apparatus used to form a strainable network into the topsheet base material.

A suitable process for forming a strainable network into the topsheet 42 is described in U.S. Pat. No. 5,518,801 entitled "Web Materials Exhibiting Elastic-Like Behavior" which issued to Chappell, et al. on May 21, 1996. FIG. 7 is a simplified illustration of an apparatus used to form a strainable network into the topsheet base material. The apparatus 700 shown in FIG. 7 comprises a pair of intermeshing toothed rolls 702 and 704. In one non-limiting embodiment, the SELFing process utilizes generally triangular-shaped "teeth" 706 that are rounded at the top. The teeth 706 used to create the embodiments shown in FIG. 6 are 2.5 mm in height, and are spaced so that the peaks of the teeth are 0.6 mm apart, and there are 6.5 teeth per cm. The rolls 702 and 704 may have bands 708 around their circumference that are not provided with teeth 706 in order to leave an unformed region in the base material.

Figure 8:
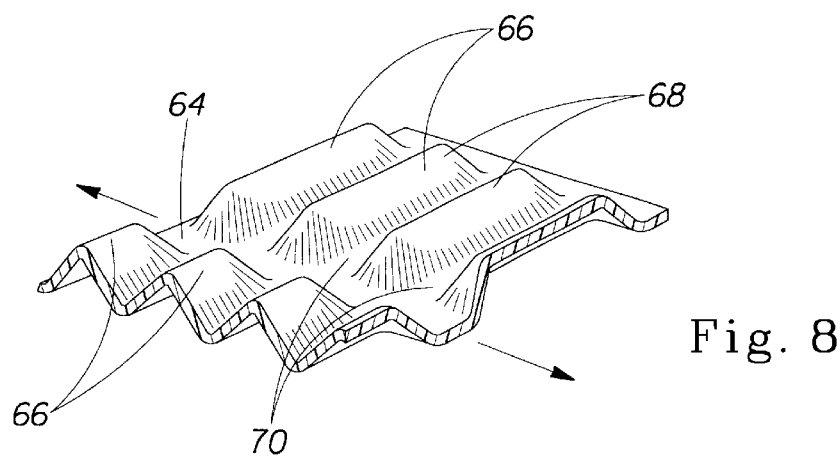
FIG. 8 is a segmented schematic perspective illustration of a portion of a web of material having a strainable network formed therein.

FIG. 8 is a segmented schematic perspective illustration of a portion of a web of material having a strainable network formed therein. This web is shown as being made from a continuous, planar base material (similar to the way in which a film would appear), rather than a plurality of fibers as are nonwoven materials. This was done so that the pattern of the strainable network would be more visible. As shown in FIG. 8, the strainable network comprises a plurality of corrugations 66 that define ridges and valleys. The corrugations 66 are separated by a generally planar region 64 that is oriented perpendicular to the ridges and valleys. The web material having the strainable network therein is extensible in the direction of the arrows.

As shown in FIG. 6, when the nonwoven material has just been subjected to the SELFing process, it has an appearance that looks similar to the schematic illustration shown in FIG. 8. However, after handling, processing and assembling the SELFed nonwoven material into the interlabial device, the nonwoven topsheet loses some of its corrugated character and is less able to maintain this appearance (or clearly defined corrugated structure). Nevertheless, without this clear definition, the ability of the nonwoven to deform under compression and motion are still present. While the compression and flexibility characteristics are less than those of a SELFed film, the SELFed nonwoven material has been found to be considerably more comfortable.

Applying a SELFing technique to the nonwoven web delivers a significant comfort improvement. Without wishing to be bound by any particular theory, the SELFing process imparts structure (hills and valleys), reducing the overall surface area of topsheet in contact with the hydrous body tissues (in this case, the labial membrane). In addition, the SELFing imparts stretchability, compressibility and opens the web up thereby reducing capillary suction via increasing the fiber-fiber distances so that the areas of the topsheet that do actually interact with the labial membrane (via capillary suction) are more free to adapt with the labial membrane without exerting capillary suction on these portions of the labial membrane. Such mechanical treatments provide micro slippage points that significantly reduce the usual adhere-shear process (tendency of the topsheet to adhere to the body, and then be sheared from contact with the body) during bodily motion that drives discomfort while wearing a pad interlabially.

Alternative processes for ring rolling or "pre-corrugating" the base material are described in U.S. Pat. No. 4,107,364 issued to Sisson on Aug. 15, 1978; U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

The webs which are used for the starting materials can be ring rolled or SELFed in one or more directions. For example, the webs can be ring rolled or SELFed in both the longitudinal and transverse directions (in the finished product). If the webs are ring rolled or SELFed in one direction, they will be extensible in one direction (perpendicular to the corrugations). If the webs are ring rolled or SELFed in two directions, they will be extensible in two directions. The embodiment shown in FIG. 6 is SELFed in only one direction.

Another suitable type of topsheet 42 comprises a mechanically altered (using SELFing or ring rolling) apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films that may be mechanically altered to form a more comfortable topsheet are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; U.S. Pat. No. 4,637,819 entitled "Macroscopically Expanded Three-Dimensional Polymeric Web for Transmitting Both Dynamically Deposited and Statically Contacted Fluids From One Surface to the Other", which issued to Ouellette, et al. on Jan. 20, 1987; U.S. Pat. Nos. 4,609,518 and 4,629,643 both issued to Curro, et al. on Sep. 2, 1986 and Dec. 16, 1986, respectively; U.S. Pat. No. 5,006,394 entitled "Multilayer Polymeric Film" issued to Baird on Apr. 9, 1991; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996).

Figure 9:
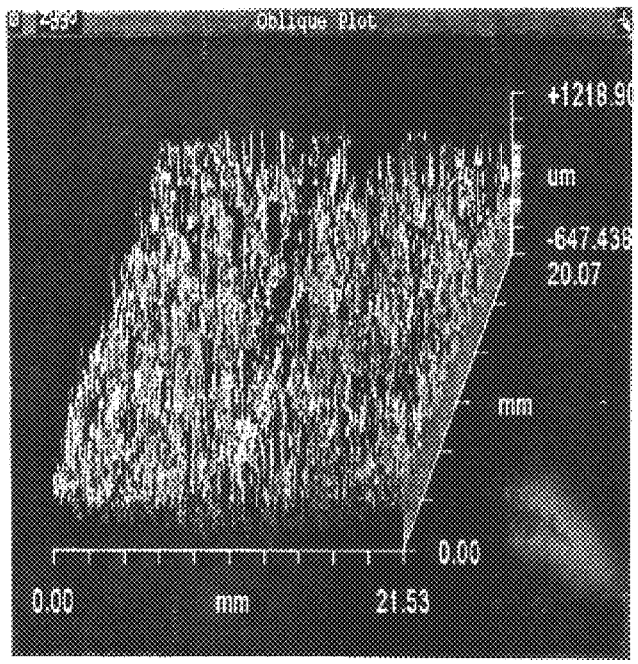
FIG. 9 is a scan of the surface of the topsheet material shown in FIG. 6.

FIG. 9 is a scan of the surface of the topsheet material shown in FIG. 6. FIG. 9 shows that the topsheet material of a preferred embodiment described herein has an irregular and three dimensional character to its surface. This can be contrasted with FIG. 10, which is a scan of a prior art rayon nonwoven topsheet material. The three dimensional surface structure of the topsheet material shown in FIG. 9 provides the same with relatively high compressibility at the relatively low forces described above. The surface of the prior art rayon nonwoven topsheet material shown in FIG. 10 differs in that it is generally regular and planar. The prior art rayon material is relatively incompressible under the forces specified herein.

Figure 11:
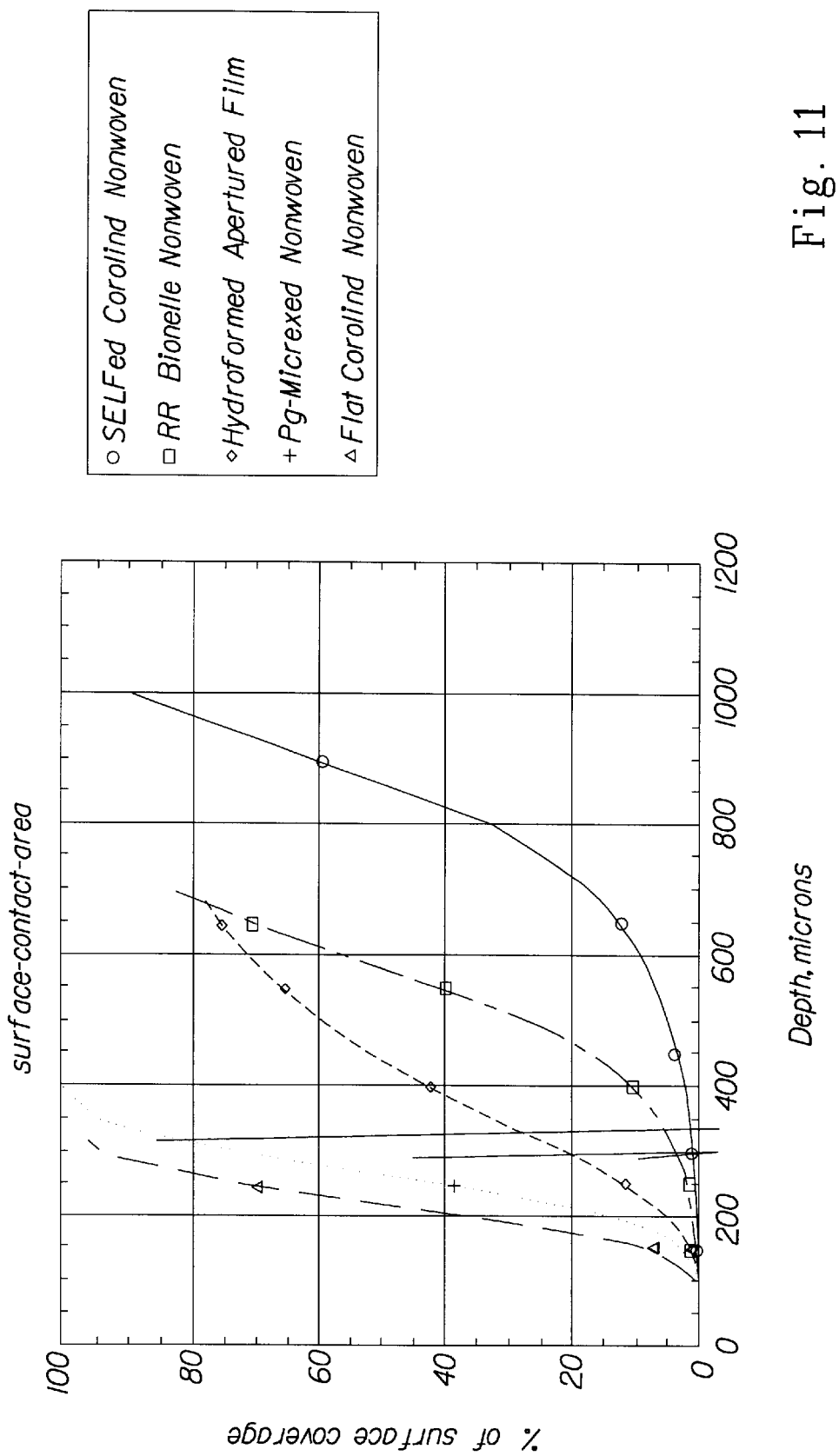
FIG. 11 is a graph of the surface area of various materials measured at various depths below the plane of their top surface.

FIG. 11 is a graph of the surface area of various materials measured at various depths below the plane of their top surface that quantifies the three dimensional character of the topsheet. The graph is a Bearing Ratio plot of various materials which can be measured according to the Surface Roughness Procedure described in the Test Methods section. This procedure takes a plane through the materials at various depths below a plane placed adjacent the highest points of the body-contacting surface of the material. A measurement is taken of the amount of the surface of the material that lies above the plane at this depth. Several topsheet materials are depicted in FIG. 11: the SELFed COROLIND nonwoven material described above; the ring rolled (RR) BIONELLE biodegradable fiber nonwoven material described above; a hydroformed apertured film, which has not been mechanically altered following hydroforming; a nonwoven material known as "P-9", which has been micrexed; a flat (non-mechanically altered) COROLIND nonwoven material; and a flat rayon nonwoven material.

As shown in FIG. 11, the amount of surface area of the SELFed COROLIND nonwoven material and the ring rolled BIONELLE topsheet material that lies above a plane that passes through these topsheets at a depth of 300 microns below the plane that passes through the highest points of their body-contacting surfaces is less than or equal to about 15% of the surface area of these topsheets as defined by the Bearing Ratio. Thus, there is much more topsheet surface area below this depth, indicating highly three-dimensional structures. The topsheets for contacting the wearer's hydrous body tissues can also be defined in that the amount of surface area that lies above a plane that passes through these topsheets at a depth of 400 microns is less than or equal to about 40%.

The topsheet 42 can be provided with at least one aperture 50 which is formed therein (that is, in addition to the spaces between the fibers of the nonwoven web) to assist in acquisition of liquids into the interlabial device 20. Preferably, the topsheet 42 is provided with a plurality of apertures. The apertures 50 can be of any suitable size and shape. There can be any suitable number of apertures. The apertures 50 can be arranged in any suitable pattern. In some embodiments, it is desirable for the apertures 50 to be distributed in an acquisition area or zone 54. The acquisition zone 54 may be of any size, but preferably occupies less than or equal to about 30% of the available absorbent surface area. The apertures 50 have a combined open area that may be any suitable percentage of the acquisition zone 54, but preferably, the combined open area of the apertures 50 is greater than or equal to 10% of the area of the acquisition zone 54. There may also be apertures outside the acquisition zone 54. Preferably, the combined open area of the apertures 50 in the acquisition zone 54 is greater than the combined open area of any apertures in the area outside the acquisition zone 54.

For purposes of illustration, FIG. 1 shows that in one non-limiting embodiment, there are twenty-six circular apertures 50, each approximately 2 mm in diameter. The apertures 50 are arranged in diagonal relationship with each other in an acquisition zone 54 that is elliptically shaped, similar to the shape of the outer edge of the interlabial device 20. In this embodiment, the absorbent core 44 surface area is approximately 2490 $mm^2$. The area of the acquisition zone 54 is approximately 520 $mm^2$. The acquisition zone 54, thus, occupies less about 21% of the available absorbent core surface area. The combined open area of the apertures 50 is 82 $mm^2$. The combined open area of the apertures 50 is about 16% of the area of the acquisition zone 54.

In another non-limiting embodiment, the apertures 50 are arranged in two longitudinally-oriented rows, one on each side of the longitudinal centerline L. There can be any suitable number of apertures in these rows. For example, these rows can be centered about the transverse centerline, T, with seven apertures in each row.

The apertures 50 can be formed in the topsheet 42 prior to assembling one or more of the components of the absorbent article, or after assembling one or more of the components of the absorbent article. For example, the apertures 50 can be formed in the topsheet material alone, and the topsheet 42 can then be joined to the other components of the absorbent article. In other embodiments, the topsheet 42 can be joined to one or more components, and the topsheet 42 and the component(s) to which it is joined are all apertured at the same time. Preferably, the apertures 50 are formed after the topsheet 42 is joined to the absorbent core 44, and both the topsheet 42 and absorbent core 44 have apertures 50 formed therein.

The topsheet 42 is preferably joined to the other components of the absorbent article in a manner so that the topsheet maintains it ability to stretch in response to the motions of the wearer's body. The inner surface of topsheet 42 may be secured in contacting relation with an underlying absorbent layer. This contacting relationship results in liquid penetrating topsheet 42 faster. The topsheet 42 may be kept in a contacting relationship with an underlying layer by bonding the topsheet 42 to the underlying layer. However, it is not absolutely necessary to bond the face of the topsheet 42 to the face of the underlying layer. The topsheet 42 can be maintained in contact with an underlying absorbent component by entangling the fibers of the underlying layer with the topsheet, by fusing the topsheet 42 to an underlying absorbent layer by a plurality of discrete individual fusion bonds, or by any other means known in the art. The topsheet can also be maintained in contact with the underlying absorbent material due to the application of the pressure of the body against the body-contacting surface of the interlabial device.

The absorbent core 44, which is best seen in FIG. 2, is positioned between the topsheet 42 and the backsheet 38. The absorbent core 44 provides the means for absorbing exudates such as menses and other body fluids. The absorbent core 44 preferably is generally compressible, conformable, and non-irritating to the user's skin. The absorbent core 44 can be of any suitable size and shape. Preferably, the absorbent core 44 has the same general shape as the overall absorbent interlabial device 20.

The absorbent core 44 may comprise any suitable material that is capable of absorbing and/or retaining liquids (e.g. menses and/or urine). The absorbent core 44 be manufactured from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, rayon including needle punched rayon, and thin layers of foam. The absorbent core 44 may comprise a single material or a combination of materials.

One preferred material for the absorbent core 44 is batt of rayon or a rayon/cotton blend. In one embodiment, the absorbent core 44 is a batt of fibers which comprises a 50%/50% blend of baled bleached cotton fibers and baled rayon fibers. A tri-lobal rayon known as GALAXY rayon available from Acordis of Mobile, Ala. USA has been found to work well for the material comprising the absorbent core 44.

Figure 12:
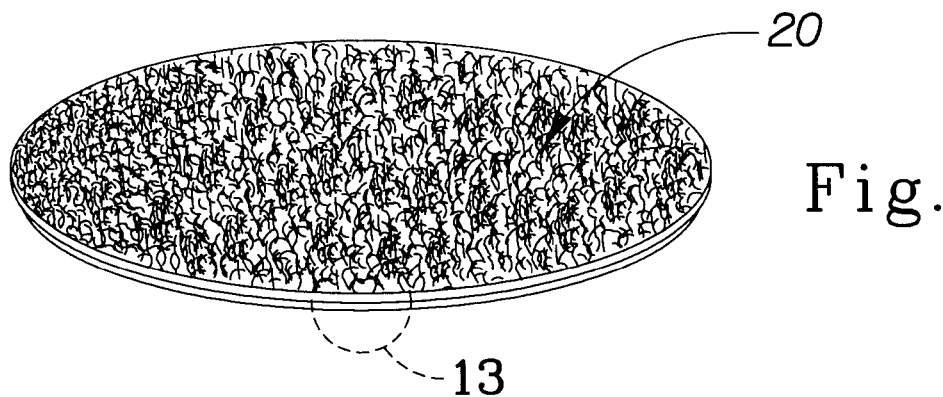
FIG. 12 is a perspective view of an interlabial device.
Figure 13:
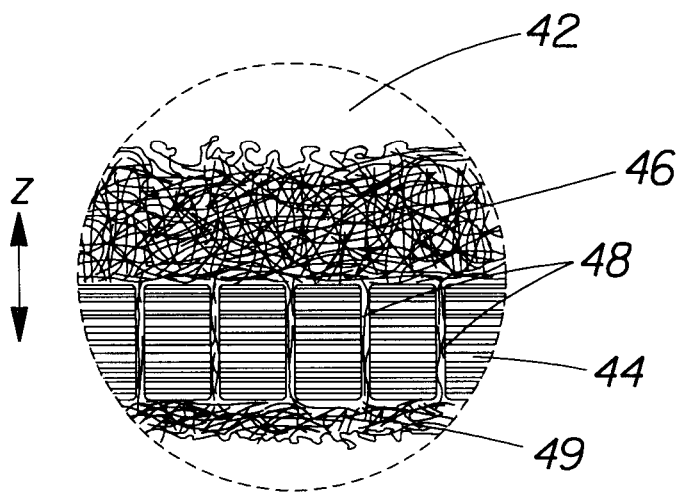
FIG. 13 is a schematic side view showing a portion of the absorbent structure of the interlabial device shown in FIG. 12.

FIG. 13 shows another preferred absorbent core structure. FIG. 12 shows the relationship of the portion of the absorbent core structure shown in FIG. 13 to the overall interlabial device. The absorbent structure shown in FIG. 13 is especially preferred when improved fluid handling is desired. The absorbent structure comprises a novel structure comprising an acquisition layer 46 and an absorbent core, or "storage core" 44, in which the acquisition layer 46 is integrated into the storage core 44 by needle punching.

The acquisition layer 46 can comprise any suitable structure that is capable of quickly taking in body fluids. Suitable types of acquisition layers are described generally in U.S. Pat. No. 5,591,149 issued to Cree, et al. on Jan. 7, 1997. In one preferred embodiment, the acquisition layer 46 comprises a high loft nonwoven web that has a fuzzy appearance. The meaning of the term "high loft" is known to those of skill in the art who deal with nonwoven materials. This fuzzy layer is designed to have a high z-direction (downward) wicking capability that is better able to contact the vaginal discharges through the apertures in the topsheet, including such discharges as blood that may be trapped or wicking within the labial membrane folds, and deliver these discharges downward to a high suction storage core 44.

One non-limiting material suitable for use as the acquisition layer 46 is a 60 g/m² carded nonwoven layer comprised of a mixture of polyethylene terapthalate (PET, a polyester) fibers and polypropylene fibers. In a preferred version of this embodiment, the acquisition layer 46 comprises about 75% by weight Celanese #295 polyester fibers obtained from Celanese AG (Summit, N.J., USA) and about 25% by weight FiberVision #163024 polypropylene fibers obtained from Fiber Visions (Covington, Ga., USA).

Another non-limiting material suitable for use as the acquisition layer 46 is a 60 g/m² carded nonwoven layer comprised of a mixture of hydrophilic and hydrophobically treated rayon to ensure efficient wicking of bodily discharges and their transport to the storage core 44 without the rayon competing with the storage core 44 to serve the function of storing the discharges. The acquisition layer 46 is comprised of 40% hydrophilic conventional tri-lobal GALAXY rayon of a 3 denier fiber containing 0.01% LEOMIN finish (known in Europe as "ASLAN") finish (a hydrophobic finish, which usually serves as a processing aid) and 60% hydrophobically-treated conventional tri-lobal GALAXY rayon of a 3 denier fiber containing 0.3% LEOMIN (ASLAN) finish, both fibers supplied by Acordis (Mobile, Ala., USA).

In a preferred non-limiting version of this embodiment, the acquisition layer comprises about 40% by weight of 40% hydrophilic conventional trilobal GALAXY rayon of a 3 denier fiber containing 0.01% LEOMIN finish supplied by Acordis (Mobile, Ala., USA) and about 60% by weight of BIONELLE 3001 biodegradable fibers obtained from Showa Hugh Polymer Co. of Tokyo, Japan or fibers that provide equivalent performance to the biodegradable fibers. The acquisition layer 46 can be manufactured and then physically combined to the storage core 44 through a needle punching process by Texel, Inc. of Quebec, Canada. As shown in FIG. 13, the needle punching process causes a plurality of vertical channels 48 to be formed in the storage core 44. There is also a portion 49 of the acquisition layer 46 that underlies the storage core 44 as a result of the needle punching process. In a variation of this embodiment, the topsheet can be combined with either of these layers by needle punching process.

The storage core 44 can comprise any suitable structure that is capable of efficiently storing the body discharges that are received from the acquisition layer 46. In one preferred embodiment, the storage core 44 comprises a 300 g/m² airlaid layer comprised of superabsorbent fibers, airfelt, and bicomponent fibers. Although the superabsorbent fibers can be distributed in any suitable manner within the storage core, the superabsorbent fibers are preferably distributed substantially uniformly throughout the storage core 44. The storage core 44 is preferably comprised of a high concentration (greater than or equal to about 25% by weight) of a fibrous superabsorbent material (or absorbent gelling material), preferably a high gel strength fibrous superabsorbent material. Traditionally, such a high concentration of superabsorbent material (particularly fibrous superabsorbent material) would not be expected to deliver efficient core performance due to gel blocking. But, using a needle punching technique (such a technique is used to make plush piled carpets, for example) the acquisition layer 46 can be vertically integrated directly into the storage core 44 (fibers from the acquisition layer in the needle punching process are driven through the storage core and anchored below). Without wishing to be bound to any particular theory, this technique ensures efficient fluid transfer from the acquisition layer 46 to the storage core 44 without flooding the superabsorbent material while the needle punched nonwoven fibers from the acquisition layer 46 actually help to keep open the storage core 44; both aspects working to avoid gel blocking.

The storage core 44 can comprise fibrous superabsorbent material in any suitable amount. Some non-limiting preferred ranges for the amount of fibrous superabsorbent material include between: about 25% to about 100%; about 25% to about 70%; and about 25% to about 50% by weight. Any ranges included within these ranges are also included. The higher concentrations of superabsorbent material specified about (e.g., above 70%), are particularly suitable if the storage core 44 comprises a relatively open high loft nonwoven material. This high loft nonwoven material could, for example, be a carded nonwoven. Alternatively, instead of comprising fibrous superabsorbent material, in less preferred embodiments, the superabsorbent material can be in the form of particles, or any other form known in the art. In other embodiments, the storage core 44 can comprise superabsorbent material in a combination of different forms.

One non-limiting material suitable for use as the storage core 44 in the integrated acquisition layer/storage core structure described above comprises about 45% FIBERDRI type 1162 superabsorbent fibers obtained from Camelot Technologies Ltd. of Alberta Canada; about 49% airfelt fluff obtained from Korsanas A-E (Sweden); and about 5–6% of 4 mm long C1.7 dtex bicomponent fiber (AL Adhesion) comprising a polypropylene core with a polyethylene sheath obtained from FiberVision of Covington, Ga., USA.

In a more preferred version, the amount of non-biodegradable bicomponent fiber is further reduced to about 4% to enhance the overall ability of the storage core to disintegrate and degrade. Alternatively, the storage core 44 can comprise biodegradable bicomponent fibers to aid in the biodegradability of the product, or alternatively a water soluble latex binder such as an EVA based latex binder type Airflex192 available from Air Products Inc. (Allentown, Pa., USA) can be used to impart integrity to the airlaid storage core 44 while delivering superior biodegradability. In one non-limiting embodiment, the storage core 44 can be manufactured on an standard thermally bonded airlaid line with two or more forming heads, which creates an integrated multi-layered structure.

In other embodiments, the absorbent core 44 may consist of multiple independent layers of the same, or different materials (such as layers of absorbent materials with different absorbent properties), that are easily separatable so the various layers can separate for disposal.

In an alternative embodiment, instead of providing the topsheet 42 with the comfort enhancing properties described herein, the topsheet 42 could be a very open material, or a very thin material, and the underlying layer, such as the acquisition layer 46 (or the absorbent core 44) could be provided with the comfort-enhancing properties of the topsheet 42 described above. Such a topsheet 42 could serve primarily to retain fibers in the underlying acquisition layer 46 or core 44. In other words, an article can be provided in which the top surface structure comprises a first component (like the topsheet 42) having apertures therein and a second component (such as the acquisition layer 46) that underlies this first component. The second component can have portions that underlie the apertures in the first component, and portions of the second component that underlie the apertures in the first component can form part of the top or body-contacting surface of the article. In other alternative embodiments, the topsheet could be omitted altogether, and the body-contacting layer could be the acquisition layer 46, or the absorbent core 44, and the acquisition layer 46 or the absorbent core 44 could be provided with the properties described herein for the topsheet (for improving the comfort of the same).

The backsheet 38, which is best shown in FIGS. 2 and 3, prevents the exudates absorbed and contained in the absorbent core 44 from wetting articles and/or body parts which may contact the absorbent interlabial device 20 such as pants, pajamas, undergarments, pubic hair, the wearer's thighs, etc. The backsheet 38 should be flexible and impervious to liquids (e.g., menses and/or urine). As used herein, the term "flexible" refers to materials which are compliant and will readily conform to the general shape and contours of the human body. The backsheet 38 also provides protection for the wearer's fingers as the absorbent interlabial device 20 is inserted, or as the device is optionally removed with the fingers.

The backsheet 38 may comprise a woven or nonwoven material, polymeric films such as thermoplastic films of polyethylene or polypropylene, composite materials such as a film-coated nonwoven material, or organic material such as a collagen film. Other suitable materials include dispersible materials such as polyvinyl alcohol, and biodegradable polymers that can be made into films and the like. Suitable biodegradable polymers include: BIONELLE 3001 obtained from Showa Hugh Polymer Co. of Tokyo, Japan; BAK 403 biodegradable polymer obtained from Bayer AG of Leverkusen, Germany; Matter Bi ZF03U-A obtained from Bicorp Co., distributor for Novamont S.P.A. of Rome, Italy; and, Biopol biodegradable polymer obtained from Monsanto. In one embodiment, the backsheet may be made from a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. Preferably, however, the backsheet 38 comprises a film having a similar thickness to this polyethylene film, only which is made of a biodegradable polymer such as the BIONELLE biodegradable polymer described above.

The backsheet 38 may also permit vapors to escape from the interlabial device 20 (i.e., be breathable) while still preventing exudates from passing through the backsheet. A suitable breathable backsheet material is a laminate of an apertured film such as that described in U.S. Pat. No. 3,929,135 issued to Thompson which is inverted so that the smaller openings of the tapered capillaries face the absorbent core 44 which is adhesively laminated to a microporous film such as that described in Exxon's U.S. Pat. No. 4,777,073.

In preferred embodiments, the backsheet 38 is dispersible and/or dissolvable in water. Polyvinyl alcohol (including co-polymers of polyvinyl alcohol) has been found to be suitable as a material for a dissolvable backsheet 38. The polyvinyl alcohol may be coated on a tissue, a nonwoven material such as a biodegradable nonwoven material (e.g. rayon), or coated with a wax, such as paraffin, or other hydrophobic coating to reduce the rate at which it dissolves in water. This allows the backsheet 38 to maintain its integrity during use, while retaining the ability to dissolve in water during disposal of the interlabial device 20.

The term "dispersible", as applied herein to an absorbent interlabial device or a component thereof, refers to an article or material which will disperse into at least two fragments in mildly agitated water. Such a device will break into pieces in a conventional toilet and/or domestic plumbing system, and will ultimately be effectively processed though a sewage treatment system. The term "dissolvable", as applied herein to an absorbent interlabial device or a component thereof, refers to an article or material which will at least partially dissolve and essentially assume liquid form or otherwise be indistinguishable to the naked eye from the liquid medium in which it is dissolved.

Figure 4:
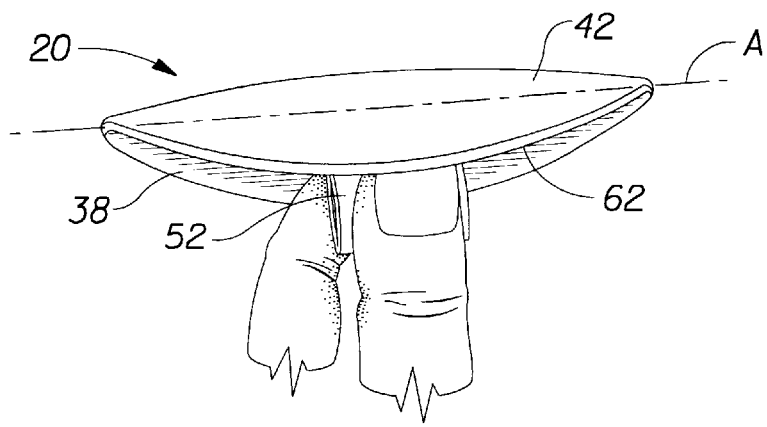
FIG. 4 shows the absorbent interlabial device shown in FIG. 1 folded along the axis of preferred bending and being grasped for insertion by the wearer's fingers.

In other embodiments, the backsheet can be eliminated. In some embodiments, the backsheet can be eliminated if the underside of the absorbent core is coated, or otherwise treated, to make the backsheet resistant to the passage of liquids therethrough. Alternatively, when the interlabial device 20 is folded along a longitudinal axis A (as shown in FIG. 4), especially if the device is primarily contained within the labia, the underside of the two halves of the interlabial device 20 which would normally be provided with a backsheet, will contact each other (that is, after the user's fingers are removed), and the main body portion of the device 20 will assume an inverted V or U-shaped cross-sectional structure. In this case, the portion of the device 20 which would normally be provided with a backsheet will not contact a wearer's garments, so the backsheet will not be necessary. The elimination of a backsheet will improve the breathability of the device.

The components of the absorbent interlabial device 20 described above (topsheet 42, backsheet 38, if one is present, acquisition layer 46, if present, and absorbent core 44) can be assembled in any suitable manner. In the embodiment shown in FIGS. 1–3, the components of the main body portion 22 are assembled in a "sandwich" configuration with the components sized so that the edges of the topsheet 42 and backsheet 38 extend outward beyond the edges of the absorbent core 44.

The components of the interlabial device 20 can be joined together in any suitable manner. The term "joined," as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with the another element, i.e., one element is essentially part of the other element.

In the embodiment shown in FIGS. 1–3, the topsheet 42 and backsheet 38 are preferably at least partially peripherally joined using known techniques. As shown in FIGS. 1 and 2, the topsheet 42 is preferably secured to backsheet 38 along a seam 60. Seam 60 is preferably liquid impervious. The seam 60 can be formed by any means commonly used in the art for this purpose such as by gluing, crimping, or heat-sealing. The seam 60 and the area of the interlabial device 20 in the vicinity of the seam 60 should be soft, compressible, and conformable. If the seam 60 and surrounding area are too stiff or non-compressible, the wearer may experience discomfort when wearing the interlabial device 20.

In addition to the peripheral seam, the components of the absorbent interlabial device 20 can be joined together at their faces. The faces of the components of the interlabial device 20 can be joined together by adhesives, stitching, heat and/or pressure bonds, dynamic mechanical bonds, ultrasonic bonds, intermingling or entanglement of the fibers or other structural elements comprising the components of the absorbent interlabial device 20, such as by meltblowing the fibers comprising one component onto another component, extruding one component onto another, or by any other means known in the art. The components of the absorbent interlabial device 20 may be joined with water soluble adhesives in order to increase the tendency of the device 20 to disperse into a plurality of fragments in mildly agitated water (such as in a toilet). It is, therefore, desirable that the material joining the components lose strength when exposed to an excess of water, such as when placed in a toilet. Water soluable or water dispersible adhesives, such as those based on carboxymethyl cellulose, polyvinyl alcohols, starches, and the like are well known in the art.

The absorbent interlabial device 20 is preferably provided with an optional insertion and/or removal tab 52 joined to the underside 20B of the main body portion 22. The tab 52 may be of any suitable size which provides for a convenient finger grip during insertion and, optionally, removal of the device 20. In the embodiment shown in FIGS. 1–3, the tab 52 is about 20 mm long, and about 13 mm in height (i.e. measured in the "z"-direction after attachment). The tab 52 provides an element for the wearer to grasp the device 20 during insertion. The absorbent interlabial device 20 is designed to be expelled by urination. The tab 52, however, may provide an alternative mechanism for removal of the device 20 (i.e. removal with the fingers). The tab 52 may be made of a variety of materials and need not be absorbent. In one example, the tab 52 may be formed from a nonwoven material which is heat bonded to a tissue layer. A suitable nonwoven material is known as COROLIND and is available from BBA Nonwovens, Peine, Germany, the same material used for the topsheet prior to mechanically altering the same. A suitable airlaid tissue is available from Merfin Hygenic Products, Ltd., of Delta, British Columbia, Canada, having a basis weight of about 61 g/m$^2$ and having the designation grade number 176.

Preferably, the interlabial absorbent device 20 of the present invention is toilet-disposable. The term "toilet-disposable", as used herein, means that the interlabial device is capable of being disposed of in a toilet. The interlabial device is preferably at least flushable. In particularly preferred embodiments, the interlabial device may also be provided with one or more of the following characteristics: dispersibility, settleability, disintegrateability, and biodegradability.

As used herein, the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an absorbent interlabial device, is set out in the Test Methods section of this specification.

Preferably, the absorbent interlabial device 20 of the present invention is dispersible and will disperse into at least two fragments within two hours of exposure to mildly agitated room temperature water as described in the Water Dispersion Test in the Test Methods section, below. More preferably, the interlabial absorbent device 20 will be dispersed into a plurality of fragments within about 60 minutes or, even more preferably within about 30 minutes, and most preferably, within about 15 minutes as measured by the Water Dispersion Test. Preferably, the product will break into fragments which individual fragments are smaller than about 6 in$^2$, more preferably smaller than about 4 in$^2$, most preferably smaller than about 2 in$^2$. In particularly preferred embodiments of the present invention, each of the components of the interlabial absorbent device 20 will disperse into a plurality of fragments when immersed in mildly agitated water. Alternatively, the components of the absorbent interlabial device 20 may separate from each other without themselves breaking into a plurality of fragments (e.g. the topsheet 42, backsheet 38, and core 44 may break apart from each other while each otherwise remaining intact).

"Settleability" refers to the tendency of an absorbent interlabial device, such as absorbent interlabial device 20 to eventually settle to the bottom of a septic tank or other sewage treatment system rather than to float on the surface of such tanks or sewage being processed.

Disintegrateability and biodegradability can be measured in accordance with the 28 Day Sludge Test which is contained in the Test Methods section of this specification. Preferably, the absorbent interlabial device 20 comprises biodegradable materials. While biodegradable materials are preferred for the absorbent interlabial device 20, it is not necessary that each and every material used be biodegradable. For example, the device 20 may comprise superabsorbent particles which do not biodegrade, and this will not affect the ability of the overall device 20 to remain toilet-disposable and to be effectively processed in a sewage treatment system. On an overall weight basis, the interlabial device 20 is preferably at least about 70% biodegradable, more preferably at least about 80% biodegradable, more preferably still at least about 90% biodegradable, and most preferably, at least about 95% biodegradable.

The absorbent interlabial device 20 as shown in its fully assembled configuration, preferably comprises at least one axis of preferred bending A. The axis of preferred bending A is preferably located generally along the longitudinal centerline L of the absorbent interlabial device 20. The axis of preferred bending A is a line or axis along which the absorbent interlabial device 20 will tend to bend or fold when subjected to compressive forces F directed inwardly in the transverse direction at the sides 32 of the device 20. The axis of preferred bending A may result naturally from the product configuration, or the device 20 may be imparted with a weakened axis or region in any or all of the topsheet 42, backsheet 38 and core 44 to create the axis of preferred bending A. Such a weakened axis may be created by any variety of known techniques such as scoring, pre-folding, slitting, or the like. The absorbent interlabial device 20 may comprise a region of preferred bending made up of a plurality of axes of preferred bending. Any number of such axes may comprise such a region of preferred bending up to an infinite number.

The absorbent interlabial device 20 is folded along the axis of preferred bending A, as shown in FIG. 4, prior to insertion within the wearer's interlabial space. Once inserted, the device 20 will preferably tend to unfold slightly keeping the topsheet 42 of the device 20 in contact with the inner walls of the wearer's labia. The device 20 may be resiliently biased slightly along the axis of preferred bending A to increase the tendency of the device 20 to unfold. This allows the folded device 20 to act as a "spring" under both wet and dry conditions and, consequently, to increase the tendency of the topsheet 42 of the device to remain in contact with the inner surfaces of the labia when the absorbent interlabial device 20 is in place. A device 20 constructed according to the preferred embodiment described above, however, does not necessarily require any additional structural features to provide the ability to maintain such contact.

The absorbent interlabial device 20 described herein is preferably both flexible and compressible. Flexibility and compressibility are important to product comfort. If the absorbent interlabial device 20 is too flexible, the device is not conveniently or easily placed between the folds of the labia, if it is too stiff, the device is uncomfortable and when the user is in a sitting position, the product can be forced forward against the clitoris causing discomfort.

The absorbent interlabial device 20 shown in FIGS. 1–3 (i.e. one in which the device is tapered at the ends) allows the device to easily and comfortably fit the wearer's interlabial space. A device 20 with such a tapered shape, when folded along an axis of preferred bending A (as in FIG. 4) will have a profile in which highest point along the axis of bending A (as measured in the "z"-direction) is in the vicinity of the center of the device 20 rather than at the ends. The folded configuration of the device 20 when properly sized as described above allows for consistent coverage of the walls of the labia and the vaginal introitus. Such coverage substantially reduces the incidence of "by-pass" around the device 20 by menstrual or other bodily discharges which are exhibited by previous interlabial pads.

The configuration of the absorbent interlabial device 20 is also responsible for improved product performance. As described above, there is a reduced likelihood of body or clothing soiling from discharges which are absorbed by the device 20. Additionally, when the device 20 is folded along the axis of preferred bending A, the interlabial device 20 will form a recess 62 which protects the wearer's fingers from soiling when the device 20 is inserted.

The absorbent interlabial device 20 (with or without a backsheet) may also be worn in combination with the absorbent article, such as a sanitary napkin or a pantiliner. In such a case, the absorbent interlabial device 20 will keep the sanitary napkin or pantiliner cleaner, allowing the wearer to wear the sanitary napkin or pantiliner longer than usual.

Previous interlabial pads have not provided the attributes of the device 20 shown and described herein, and are thus not able to obtain the performance and comfort results described herein. Several previous pads consisted of a small generally cylindrically shaped absorbent material which is inserted into the interlabial space. These devices are characterized by a less clean insertion and removal and may be associated with increased panty and body soiling in comparison to the present device 20.

Other previous pads were much larger than the device 20 described herein and included significant portions which resided externally to the interlabial space. Such designs may also lead to increased body soiling as discharged bodily fluids migrate to the external surfaces of such pads. Additionally, the interlabial device 20 described herein is believed to offer comfort advantages (e.g. reduced wearing awareness) as compared to the above-described larger prior art pads. These and other interlabial devices were not sufficiently flexible, and did not simultaneously cover both labia when the wearer moved in certain manners (e.g. when the wearer squatted), and therefore, such devices did not conform to and spread with the labia. This resulted in less efficient collection of bodily exudates. Still other interlabial devices were folded and retained in a folded configuration. This would prevent such devices from opening and closing to conform to the labia when the wearer moved.

The absorbent interlabial device 20 also better conforms to the labial vault than previously available interlabial pads. Additionally, the generally flat and folded configuration of the absorbent interlabial device 20 described herein is found to give a better visual indication to users as to how to insert and use the device. Therefore, the absorbent interlabial device 20 is associated with an easier and more accurate insertion as compared to previous interlabial pads.

As previously discussed, the absorbent interlabial device 20 is designed to be placed within the interlabial space of a wearer. As shown in FIG. 4, to use the absorbent interlabial device 20, the wearer grasps the tab 52 of the device 20. If the device 20 is not provided with a tab 52, the wearer may hold the folded device 20 at the sides 32 and begin insertion. As shown in FIG. 4, the device 20 is then further inserted by pushing with a finger or fingers in the recess 62 formed by the folded backsheet 38. Recess 62 covers the tips of the wearer's fingers during insertion. This feature provides for a hygienic insertion of the absorbent interlabial device 20 of the present invention. The wearer may assume a squatting position during insertion to assist in spreading the labial surfaces.

Figure 5:
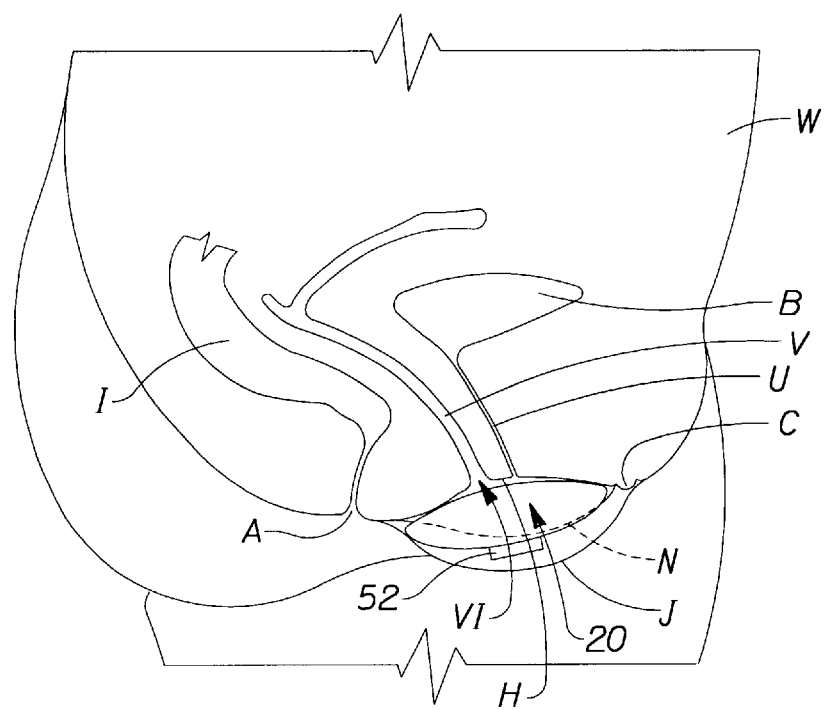
FIG. 5 is a cross-sectional saggital view of a human female wearer showing the placement of the absorbent interlabial device in the wearer's interlabial space.

FIG. 5 shows the absorbent interlabial device 20 inserted into the interlabial space of a wearer W. The urogenital members shown in FIG. 5 include the bladder B, the vagina V, the urethra U, the clitoris C, the large intestine I, the anus AN, the vaginal introitus VI, the hymeneal ring H, the labia minora N, and the labia majora J. FIG. 5 shows the relationship of these anatomical features of the wearer W to the absorbent interlabial device 20 when the device is properly inserted for use. Once the absorbent interlabial device 20 is inserted, the topsheet 42 tends to remain in contact with the inside surfaces of the labia. When the wearer is standing, the labial walls close more tightly around the folded absorbent interlabial device 20.

Other embodiments of the interlabial device 20 are also possible. Non-limiting examples of other suitable configurations for the interlabial device are contained in U.S. Pat. No. 5,762,644 entitled "Toilet-Disposable Absorbent Interlabial Device", which issued to Osborn, et al. on Jun. 9, 1998, the disclosure of which is incorporated by reference herein. The interlabial devices described in this patent may comprise a central absorbent portion and a pair of flexible extensions joined to the central absorbent portion. The flexible extensions preferably extend downwardly and laterally outward from the upper portion of the main absorbent portion, and are preferably capable of maintaining contact with the inside surfaces of the wearer's labia majora.

The interlabial device 20 is preferably at least partially retained in place by exerting a slight laterally outwardly-oriented pressure on the inner surfaces of the wearer's labia minora, labia majora, or both. Additionally, the product may also be held in place, to a degree, by attraction of naturally moist labial surfaces to the material comprising the topsheet 42. Optionally, the interlabial device 20, or any suitable portion thereof, such as at least one body-contacting surface of the interlabial device, can have a substance thereon to assist the interlabial device in staying in place in the desired position in the interlabial space. Preferably, the substance should comfortably maintain the interlabial device 20 in contact with the inside surfaces of the labia minora, or alternatively with the inner surface of the labia majora, or with both the labia minora and labia majora so that it remains in contact with these surfaces (on both sides of the interlabial space) unaided by the wearer's panties, or the like, when the wearer moves in a way that the labia spread (e.g., when the wearer is squatting with her feet about shoulder width apart). The topsheet can be adhered by the substance to portions of the wearer's body tissues, but top surface still has to maintain ability to stretch/adjust for motions and movements of the wearer's body. This will allow the interlabial device 20 to remain in place during wearing conditions, and will also ensure that it is contacted by a stream of urine when the wearer urinates so that it will be removed on urination or be easily dislodged by a wiping action such as with toilet paper.

Typically, the unloaded interlabial device 20 will weigh less than or equal to about 5 grams. The need for a substance to assist the interlabial device in staying in place becomes more important as the loading that the interlabial device 20 is expected to hold (that is, the weight of absorbed bodily liquids) increases. The absorbent interlabial device 20 can hold any suitable amount of bodily liquids up to its absorbent capacity specified above. As the weight of absorbed bodily liquids increases, the force of gravity on the loaded interlabial device increases. This results in the need for increased ability to hold the interlabial device 20 in place, particularly when the exudate loading is greater than or equal to about 8 grams (e.g. 8, 10, 12, or 15 grams). Thus, for example, if the unloaded interlabial device 20 weighs 2 grams, and is expected to hold 10 grams of bodily exudates, the interlabial device 20 must stay in place under a force of 12 grams. Also, in some instances as the interlabial device 20 becomes loaded, if it is of a configuration which has flexible extensions, one of the flexible extensions may separate from the labia adjacent thereto while the other flexible extension remains adhered to the adjacent labia. This leads to an increased risk of soiling the wearer's undergarments and/or outer garments at heavier loadings because of the possibility that bodily exudates could travel past the side of the interlabial device that is no longer in contact with the wearer's labia.

The substance used for holding the interlabial device 20 in place should have sufficient strength for holding the device securely in place, particularly against the naturally moist surfaces of the interlabial portion of the wearer's body. It should also be a material that allows the interlabial device 20 to be capable of removal without pain or trauma to the user. Preferably, the substance for holding the interlabial device 20 in place holds the device in place under the desired loadings as described above, but permits the interlabial device to be expelled from the interlabial space into the toilet when the wearer urinates. The substance, therefore, need not be adhered so that is capable of withstanding fluid pressures from the urethra of greater than or equal to about 100 centimeters of water. That is, it need only be able to withstand a pressure that is between the weight of the device when loaded up to a pressure of less than about 100 centimeters of water. (A pressure of 170 centimeters of water is the approximate maximum bear-down pressure for a typical adult human female when urinating.)

The substance for holding the interlabial device 20 in place preferably has certain additional characteristics. It should allow the interlabial device 20 to be easily placed in the proper position without discomfort, and worn without irritation. It should also preferably be biodegradable so that it is suitable for disposal in a toilet. The presence of the substance should also not interfere with the flushability of the interlabial device, if the interlabial device is of a flushable design. Preferred substances for holding the interlabial device in place are those which provide resistance to detachment under shear forces (such as those acting when the wearer walks), but can be comfortably removed using peeling forces.

The substance for holding the interlabial device 20 in place can include materials which are typically identified as adhesives, as well as materials which are not generally considered adhesives (that is, non-adhesive substances). Suitable adhesives include pressure sensitive adhesives and tacky non-pressure sensitive adhesive substances. Suitable pressure sensitive adhesives include silicone-based pressure sensitive adhesives such as polysiloxane, modified polysiloxanes, hydrocolloid-based adhesives, starch-based adhesives, and moisture-activated adhesives.

Preferably, the interlabial device is provided with a non-adhesive substance on its body-contacting surface to hold the interlabial device in place. The non-adhesive substance can be of a type that has a "tack" (that is, stickiness), or it can be of a type that does not have a "tack". Suitable non-adhesive substances include waxes (such as microcrystalline waxes, paraffinic waxes, silicone waxes, polyethylene waxes), fatty alcohols, high molecular weight alcohols, fatty acids, petroleum jelly, sealing ointments, non-ionic surfactants such as ethoxylated alcohols, ethoxylated long chain alcohols, and ethoxylated fatty acids, alkoxylated amide, alkoxylated amines, alkyl amido alkyl amines, alkyl substituted amino acids, moisture-activated substances, and combinations thereof. Another suitable non-adhesive substance is the fat substitute OLEAN manufactured by the Procter & Gamble Company of Cincinnati, Ohio under U.S. Pat. No. 5,085,884 issued Feb. 4, 1992 and U.S. Pat. No. 5,422,131 issued Jun. 6, 1995, both to Young, et al. and U.S. Pat. No. 5,422,131 issued to Elsen, et al. Without wishing to be bound by any particular theory, it is believed that such materials may hold an object in place due to high viscosity or surface tension.

Moisture-activated substances are substances which have little or no initial tack (that is, they will be dry to the touch), but when contacted by moisture (preferably relatively small amounts of moisture), they become viscous and develop a tack. Preferred moisture-activated materials for use in the present invention lose most of their tack when flooded with an excess of moisture such as when the wearer urinates. Moisture-activated substances are particularly preferred for use with the interlabial device 20 because they can make the interlabial device easier to apply than pressure sensitive or tacky adhesive-coated devices because the product does not adhere to the body as it is inserted and because it is not necessary for the wearer to spread her labia and risk soiling her hands when placing the interlabial device as may be necessary when adhesives are used. In addition, moisture-activated substances will not tend to stick to the wrong portions of the wearer's body when the product is placed between the labia and become mis-oriented, as will adhesives. They are also particularly useful for holding the interlabial device securely against this portion of the wearer's body since moisture is naturally present. In other words, they are capable of hydrating in vivo.

Some particularly preferred moisture-activated substances are polyethylene glycols ("PEGs"), sodium carboxymethylcellulose (preferably USP (U.S. Pharmacopia) grade), alcohols, glycols (dihydric alcohols) such as propylene glycols, hexylene glycols, polyols which contain three or more hydroxyl groups, such as glycerin, and sugar alcohols and other molecules capable of hydrogen bonding by contact with the water in the interlabial region, surfactants such as polyoxyl alkylates (polyoxyethylene sterates), ethoxylated alcohols, sugar surfactants, and sugars (such as glucose, fructose, and sucrose), or combinations or mixtures thereof. The foregoing substances may be used alone, in combination with each other, such as in combination with polyethylene glycols, or in combination with pectin, guar gum, locust bean gum, hydroxypropyl guar gum, polyglucomanum gum, cationic guar gum, anionic guar gum, alginate, xanthan gum, or combinations or mixtures thereof, and combinations or mixtures thereof with polyhydric alcohols.

Polyethylene glycols $(HO-(CH_2CH_2-O)_n-H)$, also abbreviated as PEG's, are substances like those found in cough syrups to coat a person's throat. Polyethylene glycols are available from Union Carbide under the trademark CARBOWAX. PEG 200 to PEG 600 (PEGs with molecular weights between 200 and 600) are liquid at or below 80° F. (27° C.). PEG 900 to PEG 20,000 and above are solid at or below 80° F. (27° C.). All are at least 60% soluble in water at 20° C. Preferably, the higher molecular weight PEG's which are in solid form are used. However, the lower molecular weight PEG's can also be used. Polyethylene glycols can be applied to the body-contacting surface of the interlabial device using any conventional processing steps, which are described in greater detail below. Once applied, they will typically dry to a non-tacky powder form. Polyethylene glycols, since they are water soluble, are also capable of losing their tendency to stick to the labia when the wearer urinates, so the interlabial device will be expelled by urination as intended. Their water solubility also ensures that they will not interfere with the ability of flushable interlabial devices to flush down a toilet, and will not float in the toilet as will some other products. (The tendency for other products to float reduces the ability of the products to go down the toilet when flushed and results in an extremely inconvenient situation for users who have to remove such products from the toilet bowl, and then dispose of these products.) Polyethylene glycols are also biodegradable, unlike most pressure sensitive adhesives, which are silicon-based.

One particularly preferred moisture-activated substance comprises a mixture of 1.75 g sodium carboxymethylcellulose, USP; 0.25 g polyethylene oxide, NF; and 125 ml distilled water. The mixture is preferably applied in a total amount of 0.15 g per each interlabial device (wet weight) if the mixture is only applied to the sides of the product, or in a total amount of 0.30 g per interlabial device if the mixture is to be applied to the entire body-contacting surface of the product.

The substance for holding the interlabial device 20 in place can be combined with other substances before it is applied to the interlabial device. Such other substances can serve as a component of the substance for holding the interlabial device in place, or as a carrier for the substance for holding the interlabial device in place. Non-limiting examples of substances that can serve in either of these manners are lotions, emollients, and mineral oil. For example, the substance for holding the interlabial device in place can be a polyethylene glycol that is mixed in a lotion formula that provides lubricity during the insertion process and develops tack when contacted by moisture. In another example, an emollient can be used as a carrier for PEG's which are in particulate form. In still another example, the PEG's can be in liquid form, and can serve as a carrier for other materials. Such other materials may include, but are not limited to, spermicides.

The substances described above can be applied to the body-contacting surface of the interlabial product (or other type of device described herein) in an intermittent pattern, a continuous pattern, or in a pattern that has both continuous and intermittent portions. Applying the substances in an intermittent pattern may be useful if it is desired to minimize interference of the substances with acquisition of liquids into the interlabial device 20 since liquids can be transported into the absorbent core between the intermittent zones of the substance. Applying the substances in a continuous pattern may be useful if it is desired to use the contact that the substance makes to the wearer's body to create a barrier to the flow of exudates over the body-contacting surface of the interlabial device. However, the application of the substances in a continuous pattern should not form an impermeable barrier which prevents menses or urine from being absorbed by the interlabial device 20.

The substance can be applied in any suitable manner, such as by spraying, padding, use of transfer rolls, or by printing, such as by gravure or screen printing. The substance can be applied directly to the interlabial device, or it may be applied to another material or component which is then adhered to the desired portion of the interlabial device.

The substance can be placed on any suitable portion of the interlabial device 20. The substance can be placed on the entire body-contacting surface of the interlabial device 20, or on a portion thereof. For example, the substance can be placed on all or a portion of the body-contacting surface of the main body portion 22. If the interlabial device is of a type that comprises a central absorbent portion and flexible extensions extending therefrom, the substance can be placed on the central absorbent portion, the flexible extensions, or both the central absorbent portion and the flexible extensions. The substance can, thus, be placed on a central region of the interlabial device 20, but not on the peripheral portions of the interlabial device. More preferably, however, the substance may be placed on the peripheral portions of the body-contacting surface of the interlabial device, but not in the central region. Locating the substance in the latter manner may be advantageous if it is desired to minimize any tendency for the substance to interfere with acquisition of bodily liquids into the interlabial device 20. The substance can also be used to create a seal to prevent the flow of exudates toward the ends (and/or sides) of the device. The substance can cover any of the following percentages of the surface area of the body-contacting surface of the main body portion 22, the central absorbent portion, the flexible extensions, or the entire body-contacting surface of the interlabial device (greater than or equal to about): 5%, 10%, 20%, 30%, 40%, 50%, 60%, 70%, 80%, 90%, or 100%.

The substance can be applied to the interlabial device 20 in any suitable quantity. For these purposes, the quantity of the substance applied to the interlabial device 20 will be expressed in terms of the total product weight including the device and the weight of the substance. Preferably, the substance constitutes less than or equal to about 20%, more preferably less than or equal to about 10%, and most preferably less than or equal to about 5% of the total product weight, so as not to excessively contribute to the overall weight of the interlabial device. This permits more of the total product weight to be dedicated to providing absorbent capacity.

There are many possible specific embodiments of interlabial devices with various substances thereon for assisting the interlabial device in staying in place in the desired position in the interlabial space. The interlabial device can have one or more of the substances described herein applied thereto in any of the patterns of application described herein.

For example, the main body portion 22 of an interlabial device having the configuration shown in FIGS. 1–3, or the flexible extensions of an interlabial device described in the patent incorporated by reference herein, may be provided with a biocompatible adhesive to assist the adhesion of that portion of the interlabial device to the inside surfaces of the wearer's labia. The strength of such an adhesive should be selected to assist the absorbent interlabial device 20 in staying in place, while still allowing for reliable, and comfortable removal of the device from the wearer's interlabial space. Examples of suitable adhesives include hydrocolloids or hydrogel adhesives that are currently available in the market, and acrylic-based adhesives.

In other embodiments, any desirable combinations of the substances described herein, or combinations of patterns of application, or both may be used. One non-limiting example would be to apply a combination of an adhesive and a non-adhesive substance to the interlabial device. For example, in the case of an interlabial device having the configuration described in U.S. Pat. No. 5,762,644, issued to Osborn, et al., a polyethylene glycol can be provided on the body-contacting surface of the central absorbent portion, and a pressure sensitive adhesive can be provided on the flexible extensions. Preferably, if adhesives are used, they are applied to portions of the interlabial device that do not block or retard the flow of urine from the urethra into the absorbent interlabial device 20.

In another example, the interlabial device 20 may be provided with one of the substances described herein (such as an adhesive) around the periphery of the body-contacting surface of the interlabial device to assist the device in staying in place adjacent to the wearer's labia. The substance can be applied in a continuous or an intermittent pattern, or a pattern which is partially continuous and partially intermittent. A swelling absorbent material can be placed inside the area defined by the substance. If a complete seal with the wearer's body is desired, this swelling absorbent can be used to eliminate any gaps or void spaces that may occur adjacent to the wearer's body that may occur due to misplacement of the interlabial device relative to the wearer's labia, and create a self-sealing device. Some non-limiting examples of swelling absorbent materials include, but are not limited to superabsorbent, hydrogel forming materials, absorbent foam materials, modified cross-linked cellulosic fibers, and compressed absorbent materials, such as those used in tampons.

Figure 14:
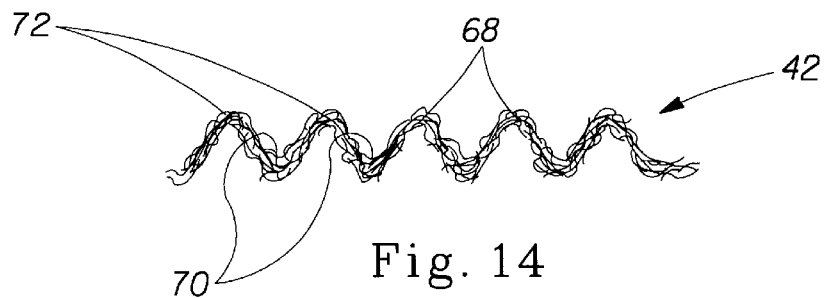
FIG. 14 is a schematic side view showing a portion of an alternative topsheet that has a plurality of ridges and valleys therein, and a substance for maintaining the topsheet in contact with a wearer's body located on at least some of the ridges on the body-contacting surface of the topsheet.

FIG. 14 shows an embodiment in which the topsheet 42 has a plurality of ridges and valleys therein. In the embodiment shown in FIG. 14, the substance for maintaining said topsheet 42 in contact with the wearer's body is located on at least some of said ridges on the body-contacting surface of the topsheet 42. The valleys, however, are preferably substantially devoid of the substance for maintaining the topsheet in contact with the wearer's body. The substance for holding the interlabial device in place is preferably only applied to ridges so that the portions of the topsheet having the substance thereon will be maintained in contact with the wearer's body, and the portions of the topsheet between the ridges will be extensible to conform to the movements of the wearer's body. As in the case of the other embodiments shown and described herein, this embodiment of the body-contacting topsheet can be used for any article that is to be placed in contact with a wearer's body, and is not limited to use on an interlabial device.

Numerous other embodiments and properties for the substance for holding the interlabial device in place are also possible. For example, the substances described herein preferably have moisture vapor transmission rates sufficient to maintain the natural state of hydration of the labial tissue. Suitable moisture vapor transmission rates are not less than about 300 gm m/hr at a relative humidity difference of 10 to 100%. In addition, any of the substances described herein can be used in conjunction with, or be combined with emollients such as those described in U.S. Pat. No. 5,609,587 entitled "Diaper Having a Lotioned Topsheet Comprising a Liquid Polyol Polyester Emollient and an Immobilizing Agent", issued Mar. 11, 1997 to Roe, and U.S. Pat. No. 5,643,588 entitled "Diaper having a Lotioned Topsheet" issued on Jul. 1, 1997 to Roe, et al.

In addition to the various embodiments of the substances for holding the interlabial device 20 in place which are described herein, the interlabial device can be provided with other optional features. For example, it has been found that the interlabial device of the present invention provides a substantial noticeable benefit to the user in controlling odors associated with body exudates. Additional odor controlling agents may be added to seek further reductions in odors. Such odor controlling agents include, but are not limited to activated charcoals, zeolites, silica, polyacrylic acids (superabsorbents), certain quaternary compounds, triethyl citrate, cyclodextrin, or any combinations thereof. Particularly preferred cyclodextrin compounds are described in U.S. Pat. No. 5,429,628 issued to Trihn, et al. and U.S. Pat. No. 5,780,020 issued to Peterson, et al. In addition, deodorants can be added to further mask these odors.

Further, over-the-counter vaginal drug actives can be added for one or more of the following purposes: cleansing, providing soothing and refreshing effects, deodorizing, relieving minor irritation, reducing the number of pathogenic microorganisms, altering pH so as to encourage the growth of normal vaginal flora, producing an astringent effect, lowering surface tension, producing a mucolytic effect, or producing a proteolytic effect. Such over-thecounter vaginal drug actives include: calcium propionate, dioctyl sodium sulfosuccinate, nonoxynol 9, octoxynol 9, potassium sorbate, povidone-Iodine (PVP-Iodine), sodium lauryl sulfate, and sodium propionate.

In these or other embodiments, the articles described herein, such as interlabial device 20, or any of the components thereof, can be made of extensible and/or stretchable materials to aid in the ability of the article to comfortably remain in place when forces are exerted on the article during wear. However, it is particularly desirable to form the interlabial device or some portion thereof from extensible and/or stretchable materials when substances are applied to the interlabial device to assist the interlabial device in staying in place in the interlabial space. For example, if the interlabial device has portions that are adhered to the labia, some extensibility is preferably present for improved comfort and to reduce the possibility of irritation. Specifically, it is desirable not to restrict the movement of the wearer's labia when the wearer's body moves. Suitable extensible materials that could be used for the components of the interlabial device, or other articles described herein, are described in U.S. Pat. No. 5,611,790 entitled "Stretchable Absorbent Articles", which issued to Osborn, et al. on Mar. 18, 1997.

Figure 15:
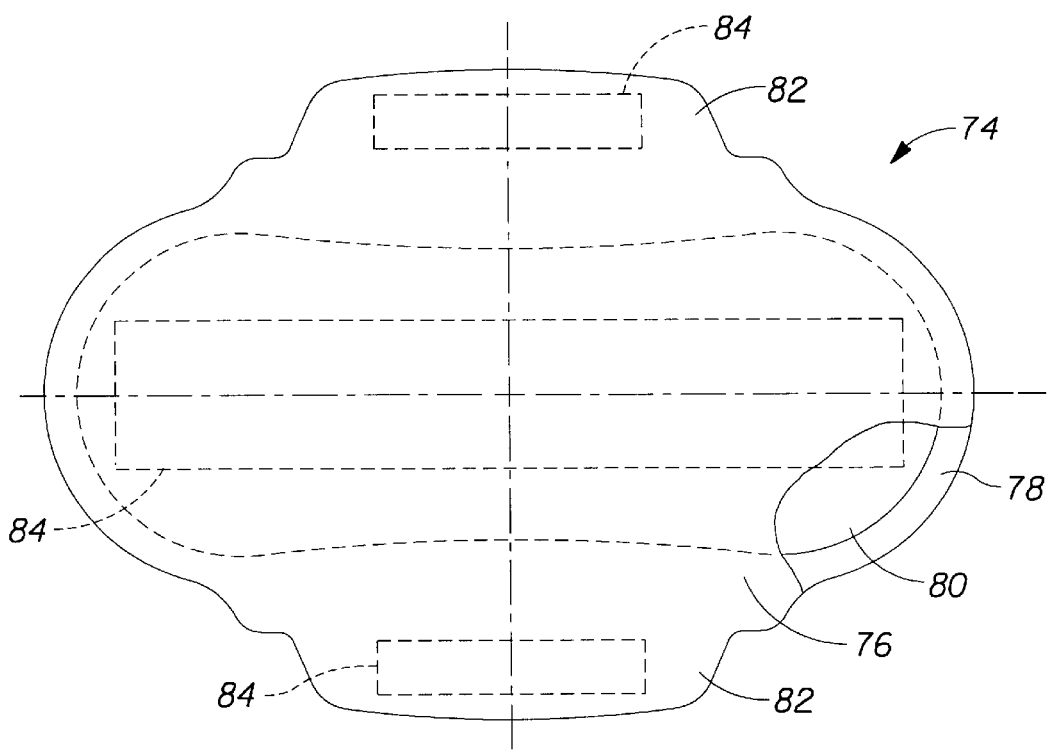
FIG. 15 is a prior art sanitary napkin which may be used in a method of using a system of feminine hygiene products or as part of a feminine protection kit with the absorbent interlabial device of the present invention.

The absorbent interlabial device 20 can be worn as a "stand alone" product. Additionally, superior performance in reducing body and clothing soiling over extended periods of wear time (such as overnight) can be obtained by using the absorbent interlabial device 20 as part of a "system" of feminine hygiene products. One such system which is effective in reducing soiling is an absorbent interlabial device, such as absorbent interlabial device 20, which is worn simultaneously with a sanitary napkin, such as sanitary napkin 70 (shown in FIG. 15).

Such a system of an interlabial device in combination with a sanitary napkin is more effective than either a sanitary napkin or an interlabial pad worn alone. The absorbent interlabial device used in such a system may, and preferably does, have all of the preferred attributes of the absorbent interlabial device 20 described above. The sanitary napkin 74 may be any suitable conventional sanitary napkin. The sanitary napkin 74 preferably comprises at least a liquid pervious topsheet 76, a liquid impervious backsheet 78 joined to said topsheet, and an absorbent core 80 positioned between the topsheet 76 and the backsheet 78. Additionally, the sanitary napkin 74 preferably includes a pressure sensitive adhesive 80 disposed on the garment facing side of the backsheet 74. The adhesive 84 allows the sanitary napkin 74 to be adhered to the crotch portion of the wearer's undergarments. When the undergarments are worn in their usual wearing position, the sanitary napkin 74 will rest adjacent the pudendal region of the wearer's body. The sanitary napkin 74 may also be provided with additional features commonly found in sanitary napkins, including "wings" or "flaps" such as wings 82. A suitable sanitary napkin for use in the above-described system is the "ALWAYS" Ultra thin Maxi with Wings sanitary napkin which is manufactured and packaged by the Procter & Gamble Company of Cincinnati, Ohio under one or more of U.S. Pat. Nos. B1 4,589,876; 4,687,478; 4,950,264; 5,009,653; 5,267,992; 5,354,400; 5,389,094; 5,489,283; 5,620,430; 5,704,930 and Re. 32,649. Other sanitary napkins are also acceptable, such as those without wings 78 and those which are not of the "Ultra-thin" type.

In order to use an absorbent interlabial device and a sanitary napkin as a system of feminine hygiene products, the wearer inserts the absorbent interlabial device into her interlabial space and places a sanitary napkin in the crotch portion of a panty-type undergarment. These two steps may be performed in either order. Some women will prefer to place the sanitary napkin in the panty crotch first in order to catch and absorb and drops of menstrual flow which might be released prior to the time that the absorbent interlabial device can be inserted. Other women will chose to first insert the absorbent interlabial device. After the absorbent interlabial device is inserted and the sanitary napkin is positioned in the undergarment crotch, the undergarment is pulled up into its usual wearing position. Consequently, the sanitary napkin will rests adjacent the pudendal region of the wearer's body and will be worn simultaneously with the absorbent interlabial device.

Preferably, the absorbent interlabial device used with the above-described system is changed each time the wearer urinates. The associated sanitary napkin may be worn during for longer periods of time (i.e. beyond the changing of the absorbent interlabial device) because the bulk of the bodily fluids will be deposited on and absorbed by the interlabial device as opposed to the sanitary napkin. Particularly if the absorbent interlabial device 20 is provided with a tab 52 for removal, some women will prefer to remove the absorbent interlabial device 20 prior to urination, then subsequently re-insert the same device 20 if it has not yet absorbed near its full capacity. In addition, if a woman chooses not to dispose of the interlabial device by flushing it down the toilet, the tab 52 provides a hygenic way for the woman to remove the product and dispose of it.

The sanitary napkin and the absorbent interlabial device of the above-described system may be packaged in a common package as a feminine hygiene "kit." Such a kit facilitates use of the system of the present invention. Preferably, the packaging associated with such a kit will include instructions on how to use the absorbent interlabial device and the sanitary napkin according to the above-described method as a system of feminine hygiene products.

Figure 16:
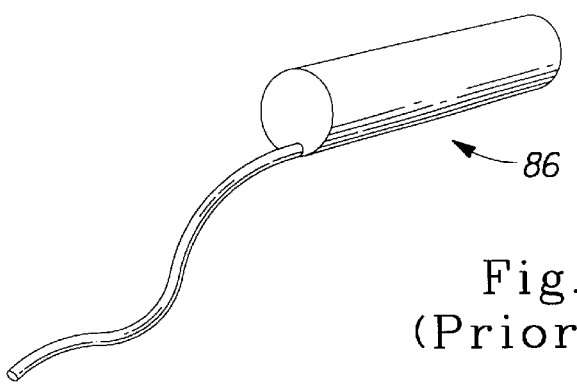
FIG. 16 is a typical prior art tampon which may be used in a method of using a system of feminine hygiene products or as part of an additional feminine protection kit with the absorbent interlabial device of the present invention.

An alternate suitable system of feminine hygiene products comprises the absorbent interlabial device 20 used simultaneously with an absorbent tampon, such as tampon 86 shown in FIG. 16. The absorbent tampon of this system of feminine hygiene products may be any suitable conventional catamenial tampon including any of the tampons sold under the trademark "TAMPAX" and distributed by The Procter & Gamble Company of Cincinnati, Ohio. The tampon used may be either of the applicator insertion or digital insertion type and any suitable applicator known in the art may be used. The tampon is first inserted into the vaginal cavity of the wearer. Following insertion of the tampon, the absorbent interlabial device is inserted into the interlabial space of the wearer. The interlabial device and the tampon are then worn simultaneously for a period of time. The absorbent interlabial device may be removed and changed each time the wearer urinates, or may be removed then re-inserted subsequent to urination.

Similarly, the absorbent tampon and the absorbent interlabial device 20 of this system may also be packaged in a common package as a feminine hygiene kit. This kit facilitates use of the alternate system described herein.

Systems and associated kits of the present invention may also comprise the simultaneous use of an absorbent interlabial device, tampon, and sanitary napkin. Kits comprising all three types of feminine hygiene products may also be packaged in a common package and include appropriate instructions for use of such systems.

In addition to the systems described above, the absorbent interlabial device 20 may be worn simultaneously with a pantiliner, or incontinence pad for menstrual or incontinence use. The absorbent interlabial device 20 described above may be combined and packaged with a pantiliner, an incontinence pad, or a sanitary napkin to form a feminine urinary incontinence kit. Such an incontinence kit preferably includes appropriate packaging material instructing the wearer as to how to use the feminine hygiene products for light incontinence protection. The interlabial device 20 can be worn in conventional panties, or it can be used with menstrual shorts.

Numerous alternative embodiments of the absorbent interlabial device. For example, these products are designed to be removed by urination, although an alternative extraction string or loop may be used. These products may also be used with emollients and/or medicinal treatments. For example, a suitable emollient composition for use on the absorbent interlabial device 20 is comprised of about 50% petrolatum (such as White Protopet 1S made by Witco Corp.), about 35% Cetearyl Alcohol (a mixed linear $C_{16}$–$C_{18}$ primary alcohol made by The Procter & Gamble Company under the name TA-1618), and about 15% Ceteareth-10 made by BASF. An emollient coating of about 0.03 g/pad has been found to be suitable.

The absorbent interlabial device 20 may be provided with a visual indication on the center of the topsheet 42 designating the area of greatest absorbent capacity of the device 20. Such an indication may consist of a differently colored region such as a pink oval. The indication may be about 12 mm wide and about 20 mm long. The absorbent interlabial device 20 may also be provided with a visual change indication. In other words, the device 20 may have a ring, bonding pattern, compression lines, or other visual indicator provided on the surface of the topsheet 42 at a predetermined distance inboard from the seam 60. When absorbed bodily discharges reach the visual change indication or outboard of the change indication, the user knows to replace the absorbent interlabial device 20. Such a change indication is particularly useful to users who remove the device 20 prior to urination and then re-insert the same device 20 if it has not yet reached its absorbent capacity.

If desired, the absorbent interlabial device 20 may be packaged in an individual package. The individual package may be comprised of a number of suitable materials, including films and toilet-disposable materials. In one embodiment, the package can be made of a film which is frangibly sealed at the edges. The package can be provided with an opening tab which can be of any suitable configuration. Suitable methods for frangibly sealing packages are described in U.S. Pat. No. 4,556,146 issued to Swanson and U.S. Pat. No. 5,462,166 issued to Minton, et al. Suitable tabs for such a package are described in U.S. Pat. No. 5,413,568 issued to Roach, et al.

It should be understood that the substances and other features and components described herein may also be applied to other types of absorbent articles, including, but not limited to diapers, sanitary napkins, tampons, incontinence devices, pantiliners, and bandages.

Test Methods

For all test methods, unless otherwise specified, standard laboratory climatic control as specified by TAPPI under T402 om-93, Section 3 (73° F. or 23° C.±1° C., 50%±2% RH) should be utilized. All samples should be acclimated to these conditions for at least two hours prior to measurements. The tests should be performed under similar conditions.

Material Critical Surface Tension

For the purposes of the present invention, the hydrophilicity or hydrophobicity of a material is to be measured by determining the material's critical surface tension. Critical surface tension is determined by applying a series of liquids of known surface tension to a material and observing the wetting behavior. The critical surface tension of a material should be measured using the ASTM method for measuring the wetting tension of polymer films, ASTM D 2578-94. This method will work with nonwoven materials as well.

Examples of critical surface tension values for several materials of interest are as follows:

| Material | Critical Surface Tension (dynes/cm) |
|---|---|
| COROLIND | 29–30 |
| BIONELLE | 40 |

Topsheet Compressibility (Thickness Change)

This test procedure determines the topsheet caliper changes under pressures. This procedure can be used to calculate topsheet compressibility (and density) as a functions of two applied pressure loads. These pressures may be typical of those found within the labial vestibule while wearing an absorbent pad interlabially. However, this procedure is intended to be used to test topsheet materials whenever topsheet compressibility is specified in the appended claims, and is not limited to testing topsheets used only on interlabial products.

Sampling

Samples should be cut such that they are larger than the 40 mm diameter circular foot that is used to compress the sample. A rectangular cutting die 10 cm by 10 cm was found to work well and to ensure no edge effects associated with irrecoverable sample compression during cutting occur. The area to be tested should be able to lie flat (preferably, less than 0.05 mm deviation in flatness). The structure of the topsheet should not, however, be altered in order to flatten the samples. Samples may be cut from a raw material roll or a finished product but the cut area must be free from wrinkles or curvature and must be representative of the undistorted dimensions of the topsheet material. The topsheet layer must be cleanly separable from other materials. At least three different samples should be measured with the average result reported.

For topsheet samples that are removed from a finished product and if the sample dimensions are not large enough to measure as described above, then a smaller diameter circular foot will need to be chosen. Provided that the applied pressure is maintained, as detailed below, and irregular edges or material damage linked to topsheet removal are avoided, the use of a smaller diameter circular foot is acceptable. If a smaller diameter foot is utilized, then a minimum of five samples should be measured to ensure a representative measurement of the topsheet surface is obtained. Ensure the topsheet is carefully removed without alteration of its surface structure.

Apparatus

This testing procedure requires an accurate (to +/−0.01 mm) thickness gauge such as a Ono-Sokki GS-503 gauge available from Ono-Sokki Technology, Inc. of Addison, Ill., USA equipped with an interchangeable circular foot. Ideally, the thickness gauge is attached to a digital readout module, such as a Ono-Sokki model DG-3610. To ensure no meaningful irregularities are present on the surface upon which samples are to be placed and measured, that would otherwise lead to measurement errors, a smoothly polished granite block (such as supplied by Rock of Ages Surface Plate, Barre, Vt., USA polished to at least 0.001 mm flatness) or equivalent should be used as the measurement surface.

Circular measurement foot:

| | |
|---|---|
| A circular flat foot of diameter = | 40.0 mm ± 0.5 mm and a weight of 10 g has been chosen. |
| Complete weight (foot + caliper shaft) = | 32 g ± 1 g. |
| Initial measurement pressure = | 250 N/m² (2.55 g/cm² or 0.036 psi) |
| Additional weight attached to shaft = | 100 g ± 1 g |
| Final weight (foot + weight + shaft) = | 132 g ± 1 g |
| Final measurement pressure = | 1000 N/m² (10.5 g/cm² or 0.149 psi) |

Procedure
1. Ensure the caliper gauge is calibrated using a standard gauge prior to commencing the measurements and accurate to ±0.01 mm.
2. Place the sample with body facing surface facing upwards on the polished granite surface with the caliper shaft and foot assembly unit positioned centrally above the sample to be tested. The test is commenced with a standard circular foot (40 mm) and a total shaft+foot weight of 32 g.
3. Gently lower the caliper shaft and foot assembly onto the sample and after waiting 5 seconds (but not more than 10 seconds) record initial sample thickness to the nearest 0.01 mm. This corresponds to the thickness under a pressure of 250 N/m² (2.55 g/cm² or 0.036 psi).
4. With the sample still positioned under the circular foot carefully place the additional weight disc (100 g) onto the caliper shaft (the total weight is now 132 g) and after waiting 5 seconds (but not more than 10 seconds) record the final sample thickness. This corresponds to the thickness under a pressure of 1000 N/m² (10.5 g/cm² or 0.149 psi).
5. The change in topsheet caliper is determined by subtracting the final caliper from the initial caliper (see calculation below).

Calculations

The change in topsheet caliper as a result of compressive forces is determined by;

Topsheet Caliper Change=Caliper (at 250 N/m²)–Caliper (1000 N/m²)

The greater the Topsheet Caliper Change number, the more the topsheet will be capable of compressing and adapting to compressive forces during during wear of the absorbent device without directly passing these forces on to the sensitive membranes of the wearer's body.

Topsheet Low Force Extensibility Test

This test procedure determines the topsheet extensibility at low elongation force.

This procedure is based on ASTM methods D 5035-95 and D 117-97a. The determination of topsheet extensibility (as a function of % elongation) in cross-machine direction or machine direction is determined using these standard methods applied with the following specific details.

Sampling

Representative samples should be cut from the topsheet material to a width of 25 mm (±0.1 mm) wide and 100 mm long using an appropriate cutting die. These samples will be tested according to the ATSM D5035-95 definition "strip test". Strip samples may be cut from a raw material roll or a finished product, but the cut area must be free from tinkles or curvature (e.g., from the raw material roll) and must be representative of the undistorted dimensions of the topsheet material. At least three different samples should be measured with the average result reported. Samples taken from products should be free from wrinkles, tears, holes or other defects, but the natural topography of the samples (e.g., corrugations and the like) should not be altered (e.g., by pulling them taut).

Apparatus

An Instron model 5564 tensile tester available from Instron Corporation of Canton, Mass., USA, or equivalent, is to be utilized for these tests. The Instron tensile tester is interfaced to a PC running WINDOWS 98® operating system and equipped with the data acquisition program MTS Test Works 4.0 ™ software (capable of up to 400 Hz sampling rate) available from Sintech, Inc. of Research Triangle Park, N.C. USA. High speed data acquisition speed is critical for accurate measurements since the materials to be measured are potentially highly extensible at low applied forces. The instrument set-up parameters utilized to determine the topsheet extensibility (as % elongation at 50 g load) are:

1. Sample clamp with 25 mm jaw.
2. Sample gauge length (separation of clamps at start of measurement) is 50 mm, or if a smaller size sample is used, the gauge length can be 25 mm.
3. Cross head speed is 50 mm/min.
4. A 10 Newton load cell is utilized.
5. Data acquisition rate is 400 Hz (400 data points/second).

Procedure

1. Ensure the Instron or equivalent tensile tester is correctly calibrated according to the manufacturer's set-up and maintenance procedures prior to commencing the measurements.
2. Samples should be prepared according to the principles of ASTM 5035-95 and cut to 25 mm±0.5 mm wide strips that are 100 mm±10 mm long. Strips are obtained aligned both to the machine direction and cross direction of the topsheet material web. If samples are taken from products, several products will be needed, and one strip should be taken which is aligned with the length of the article to be tested, and one aligned with the width. If the sample is removed from a product, a smaller sample size will be acceptable provided it is at least of the dimensions 25 mm±0.5 mm wide strips and 35 mm±0.5 mm long. In this case, a gauge length of 25 mm will need to be selected.
3. Gently insert samples into the Instron's jaw clamps positioned to a gage of 50 mm. Ensure samples are correctly aligned vertically, parallel to the direction of elongation and centered, without wrinkles or twists, within the clamps. Ensure the starting force is recording at or close to zero force. If the value exceeds 1 g, reposition the samples within the sample holding clamps.
   Start the tensile tester to commence recording the force as a function of material elongation, the test is automatically terminated at the topsheet break point. Measurements are recorded for topsheet extensibility in both the machine direction as well as the cross-machine direction.
4. The topsheet extensibility (expressed as % elongation at 50 g force) is determined by a analysis of the recorded data as detailed (see calculation below).

Calculations

The topsheet extensibility at 50 g force is determined from the data set. Given the high extensibility of these materials, it is critical to avoid irregularities associated with the sample set up at the test commencement. The sample should be minimally handled. It should be mounted in the clamp with no tension or a minimal (1 mm) amount of slack. To further minimize irregularities, all data points corresponding to a force less than 5 g are considered slack. At a load of 5 g, the gage gap is considered the zero point.

$$\begin{aligned}&\% \text{ Topsheet Elongation} \\ &\quad (\text{MD or CD}) \times 100\% \end{aligned} = \frac{\text{Sample length (at 50 g)} - \text{Slack length (at 5 g)}}{\text{Slack length (at 5 } g)}$$

The greater this number, the more the topsheet is able to deform with the motions of the wearer's body without directly passing shear forces on to sensitive body membranes.

Surface Roughness

The surface characteristics (roughness, contact area of a topsheet as a function of depth/caliper) of a range of nonwoven and film topsheets can be assessed using a Zygo New View 200 scanning white light interferometer, (Zygo Corporation of Middlefield Conn., USA) set up according to the manufacturer's procedures as detailed in the user manual.

The following equipment set up parameters are used in these analyses: 2.5× Michelson objective with a zoom factor of 0.5×, the Zygo Focus white light filter element, normal resolution data acquisition (320×240 data points), Minimum Modulation % set equal to 1, and Minimum Area Size set equal to 7. The scan length was set from 800 um to 1600 um as appropriate for the topography of the samples.

The Frequency Domain Analysis was set to do calculations in Low mode.

Additionally, the data was processed using a 5 point average low pass filter to eliminate minor surface noise. To accommodate a larger field of view, a matrix of 4×5 (set up used for the SELFed COROLIND sample) and 3×4 (set up used for the Rayon) analyses were automatically stitched together using the Zygo MetroPro v7.3.2.3.1 software with a 10% overlap (final overall analysis area was 21.53 mm×20.07 mm (SELFed COROLIND) or 16.29 mm×16.15 mm (for rayon.)).

Estimates of surface contact area of each topsheet with another surface were calculated from the surface profiles at a series of depths (or calipers). To minimize the impact of high frequency surface noise on this analysis, the data was smoothed/treated with an 11 point average low pass filter. A cylinder function was used to remove any slight global curvature of the sample due to the mounting procedure. The resulting surface was analyzed by the MetroPro Bearing Plot routine. Using the Inspector tool of the Bearing Plot, the percent surface area exposed at a depth of 100 to 1000 microns from the first surface contact point was determined. This data was plotted (% Surface contact area versus sample profile depth, in microns).

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 1 pound per square inch (6.9 Pa) load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

Water Dispersion Test

| Apparatus | |
| --- | --- |
| Shaker | Junior Orbit Shaker available from Lab Line Instruments of Melrose Park, Illinois. |
| Thermometer | 30 to 120° F. with 1 degree divisions |
| Timer | Digital stopwatch |
| Jar with Lid | 16 oz. glass jar with lid. |
| Test Setup | |
| 1. | Fill the glass jar with 300 ml. of 73 ± 3° F. tap water. |
| 2. | Set the speed on the Junior Orbit Shaker to 250 rpm according to the manufacturer's directions. |
| Procedure | |
| 1. | Hold a sample (e.g. an absorbent interlabial device 20) 3 to 4 inches (7.6 to 10.2 centimeters) above the surface of the water in the jar. Gently drop the sample onto the water surface. |
| 2. | Place the lid on the jar. |
| 3. | Place the jar into the Junior Orbit Shaker such that the jar is oriented on its side. |
| 4. | Start the Junior Orbit shaker with the on/off switch, starting the timer when the shaker is turned on. |
| 5. | Record the time required until the sample separates into at least two pieces. Separation does not include the disassociation of a few individual fibers from an otherwise intact sample. The time is the total time the sample is being shaken. |
| 6. | Repeat steps 1 through 5 with three additional samples. |

Calculation and Reporting

Calculate and report the mean and standard deviation of the water dispersibility time for the four samples tested.

Flushability Test

Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, the products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of the product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 10:
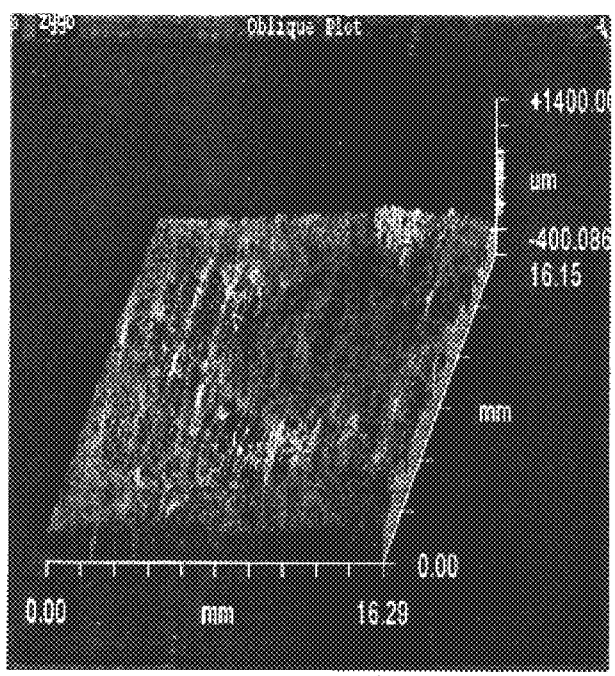
FIG. 10 is a scan of a prior art rayon nonwoven topsheet material.
Figure 17:
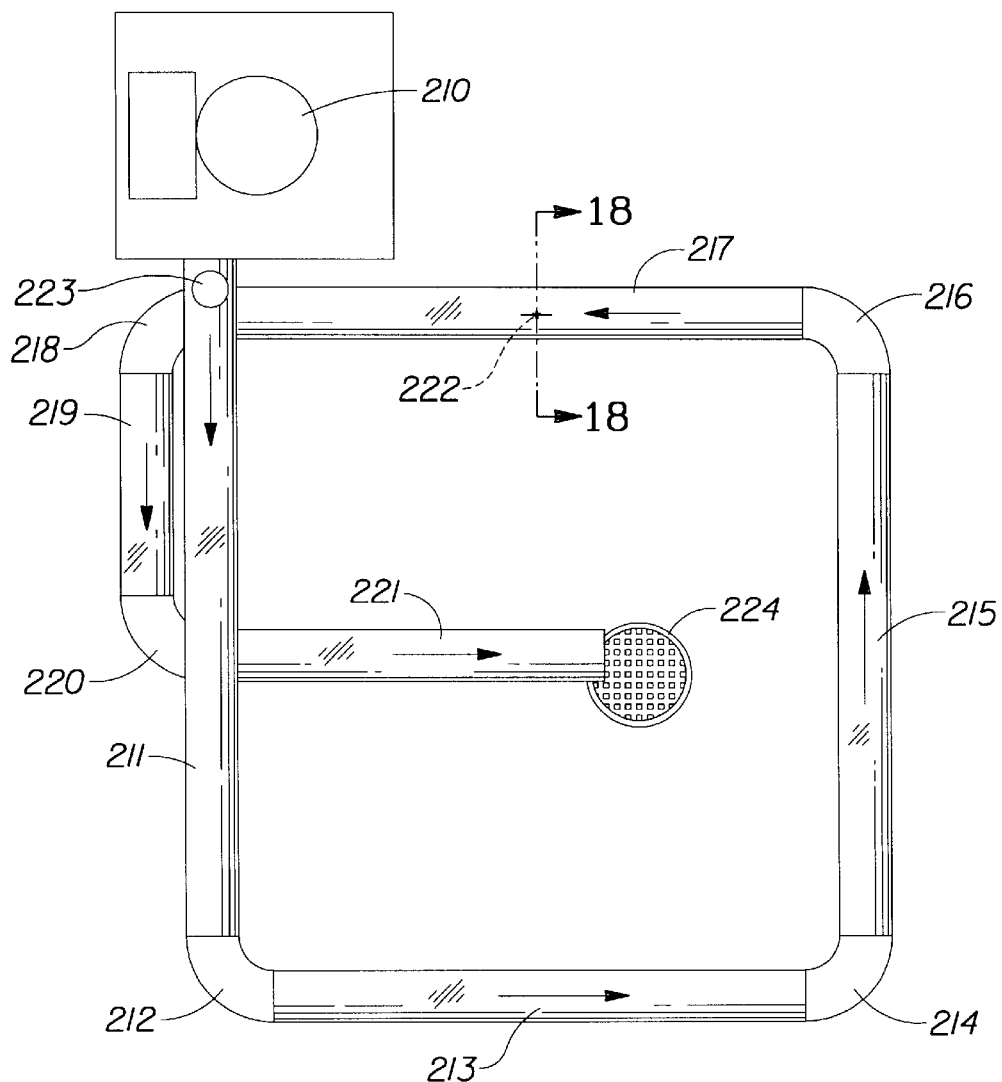
FIG. 17 is a plan view of an apparatus suitable for flushability determination according to the method described in the TEST METHODS section, below.
Figure 18:
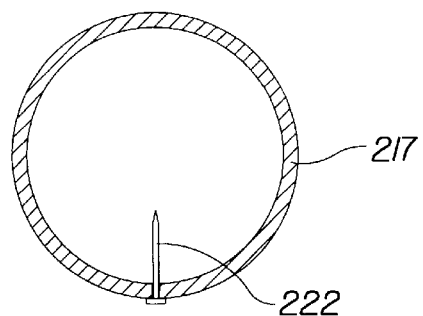
FIG. 18 is a cross-section of the flushability apparatus of FIG. 17 taken along line 18—18 thereof.

An apparatus suitable for the flushability test is shown in plan view in FIG. 10. The apparatus includes:

- a 3.5 gallon (13.2 liter) water saver siphon vortex toilet referred to as 210 (additional toilets can also be attached to the piping layout shown in FIG. 17 to evaluate the behavior of test samples using different flushing mechanisms such as commercial, pressure toilets);
- approximately 59 feet (18 meters) of 4 inch (10 cm) inside diameter acrylic pipe (As can be seen from FIG. 17, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 18) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard "CHARMIN" toilet tissue manufactured by The Procter & Gamble Company of Cincinnati, Ohio.

Synthetic Fecal Material: Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and the product to be tested and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or product is placed into the bowl, the toilet is flushed. The flushing sequence is described below as a series of two routines combined in the following order:

Routine #1 (To be performed first 6 times for a total of 30 flushes)

1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be performed 1 time)

1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of the product to clear bowl and trap in one flush
2) Incidence of failure (%) of the product to clear bowl and trap in two flushes
3) Incidence of product on simulated snag
4) Maximum level (%) of drain line blockage
5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed

Feclone synthetic fecal matter (900 grams); (Available from Siliclone Studio, Valley Forge, Pa. as product BFPS-7 dry concentrate)

Tap water at 100° C. (6066 grams)

II. Equipment Needed

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

28 Day Sludge Test

Purpose

To determine the extent to which an absorbent article disintegrates upon exposure to biologically active anaerobic sludge. Anaerobic conditions are typically found in household septic tanks, as well as in municipal sewage treatment facilities in the form of anaerobic sludge digesters. Test products, such as the absorbent article are combined with anaerobic digester sludge to determine the extent and rate of disintegration of test products over a 28 day period. Disintegration (as measured by weight change) is typically measured on days 3, 7 14, 21 and 28 of the particular study. This protocol is modeled after the National Sanitation Foundation, Ann Arbor, Mich., International Protocol: Evaluation of the Anaerobic Disintegration of a Test Product, November, 1992.

Materials

Control Product

TAMPAX Regular brand tampons will be used as a positive control product in the anaerobic disintegration test.

Material Preparation

Prior to the addition of the test and control products to the reactors, the materials will be dried in a hot air oven at 103°±2° C. for 2 hours and then weighed to determine the initial weight. Approximately equal weights of the control and the test products will be placed in respective reactors.

Anaerobic Sludge

The sludge used in this evaluation will be anaerobic sludge obtained from a municipal waste water treatment plant, or raw sewage obtained as influent from a waste water treatment plant that has been concentrated by settling and decanting the overlying water. Prior to use in the evaluation, the following parameters of the sludge will be measured in accordance with standard laboratory operating procedures:

Total solids

Total volatile solids pH

The sludge should meet the following criteria for use in the evaluation:

pH between 6.5 and 8

Total solids ≧ 15,000 mg/L

Total volatile solids ≧ 10,000 mg/L

The criteria for the activity of the sludge requires that the control tampon material must lose at least 95% of its initial dry weight after 28 days exposure.

Procedure

The test and control products are added to a 2 L wide mouth glass flask (reactor) containing 1500 ml of anaerobic digester sludge or concentrated raw sewage. Three reactor flasks per test material per sampling day are prepared. Thus, if disintegration is measured on days 3, 7, 14, 21, and 28, there will be a total of 15 reactor flasks for the test product and 15 flasks for the control product. The reactors are sealed and placed in an incubator maintained at 35±2° C. On the specified sampling days, three reactors each for the test and control material are removed from the incubator. On the designated sample days, the contents of each reactor will be passed through a 1 mm mesh screen to recover any undisintegrated material. Any collected material will be rinsed with tap water, removed from the screen and placed in a hot air oven at 103±2° C. for at least 2 hours. The dried material will be weighed to determine final weight. Visual observations of the physical appearance of the materials when recovered from the reactors will also be made and recorded.

Results

The rate and extent of anaerobic disintegration of each test material and the control material is determined from initial dry weights of the material and the dried weights of the material recovered on the sampling days. The percent anaerobic disintegration is determined using the following equation (percent weight loss):

$$\text{Percent Disintegration} = \frac{(\text{initial dry weight} - \text{final dry weight})}{(\text{initial dry weight})} \times 100$$

The average percent disintegration for the test and control products for each sampling day will be presented. For the purposes of the appended claims, the percent disintegration values are for day 28 of the study.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A body tissue-contacting topsheet for an absorbent article that is to be placed in contact with a wearer's hydrous body tissues, said topsheet comprising a non-absorbent, moderately hydrophilic to substantially hydrophobic material having an extensibility in at least one direction of greater than or equal to about 30% under a force of 50 grams, said topsheet having a critical surface tension of less than or equal to about 45, and said topsheet undergoing a caliper change of greater than or equal to about 30% when tested according to the Thickness Change Test.

2. A body tissue-contacting topsheet according to claim 1 which is three-dimensionally shaped.

3. A body tissue-contacting topsheet according to claim 1 which has a body-contacting surface, said body-contacting surface having areas of varying height, and a plane can be placed adjacent the highest points of the body-contacting surface, said topsheet having a depth, wherein the amount of surface area of said topsheet that lies above a plane that passes through said topsheet at a depth of 300 microns below the plane that passes through the highest points of the body-contacting surface is less than or equal to about 15% of the surface area of the topsheet as defined by the Bearing Ratio.

4. The body tissue-contacting topsheet of claim 2 in which the amount of surface area that lies above a plane that passes through said topsheet at a depth of 400 microns is less than or equal to about 40%.

5. The body tissue-contacting topsheet of claim 2 which comprises a nonwoven web having at least one irregular surface structure.

6. The body tissue-contacting topsheet of claim 3 comprising a mechanically altered nonwoven web.

7. The body tissue-contacting topsheet of claim 4 comprising a nonwoven web having a plurality of corrugations loosely formed therein.

8. An absorbent device insertable into the interlabial space of a female wearer comprising the body tissue-contacting topsheet of claim 1.

9. The absorbent device of claim 6 further comprising an acquisition zone with at least one aperture therein.

10. A tampon comprising the body tissue-contacting topsheet of claim 1.

11. A body tissue-contacting topsheet for an absorbent article that is to be placed in contact with a wearer's hydrous body tissues, said topsheet comprising a non-absorbent, moderately hydrophilic to substantially hydrophobic material having an extensibility in at least one direction of greater than or equal to about 20% under a force of 50 grams, said topsheet undergoing a caliper change of greater than or equal to about 40% when tested according to the Thickness Change Test.

* * * * *